United States Patent [19]
Zalkow et al.

[11] Patent Number: 6,011,058
[45] Date of Patent: Jan. 4, 2000

[54] SECO-CHOLESTANE DERIVATIVES AND METHODS OF MAKING THE SAME

[75] Inventors: Leon H. Zalkow; Hairuo Peng, both of Atlanta, Ga.

[73] Assignee: Georgia Tech Research Corporation, Atlanta, Ga.

[21] Appl. No.: 09/158,656

[22] Filed: Sep. 22, 1998

[51] Int. Cl.[7] .................... A61K 31/335; C07D 313/06
[52] U.S. Cl. .................... 514/462; 549/268; 549/280; 549/299; 558/419
[58] Field of Search ............ 558/419; 549/280, 549/268; 514/462

[56] References Cited

U.S. PATENT DOCUMENTS 4,732,897   3/1988   Cainelli et al. ................. 514/222

Primary Examiner—Deborah C. Lambkin
Assistant Examiner—Ebenezer Sackey
Attorney, Agent, or Firm—Alston & Bird LLP

[57] ABSTRACT

The present invention is directed to novel seco-cholestane derivatives, as well as to pharmaceutical compositions thereof, and methods of making the same. More particularly, the invention relates to C5- and C8-substituted seco-cholestane derivatives. The compounds of the invention can exhibit CDC25 phosphatase inhibition properties and anti-cancer activity.

48 Claims, 7 Drawing Sheets

SCHEME 1   GENERAL REACTION SCHEME FOR PREPARING THE COMPOUNDS OF FORMULA (Ia)

SCHEME 1 GENERAL REACTION SCHEME FOR PREPARING THE COMPOUNDS OF FORMULA (Ia)
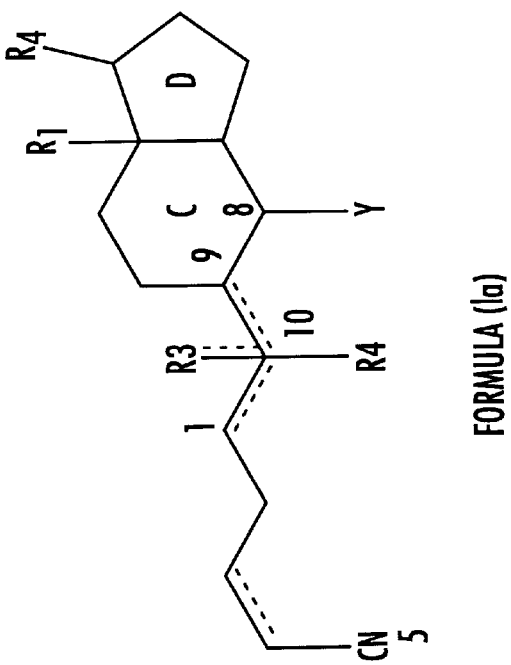
SILICA GEL / HEAT
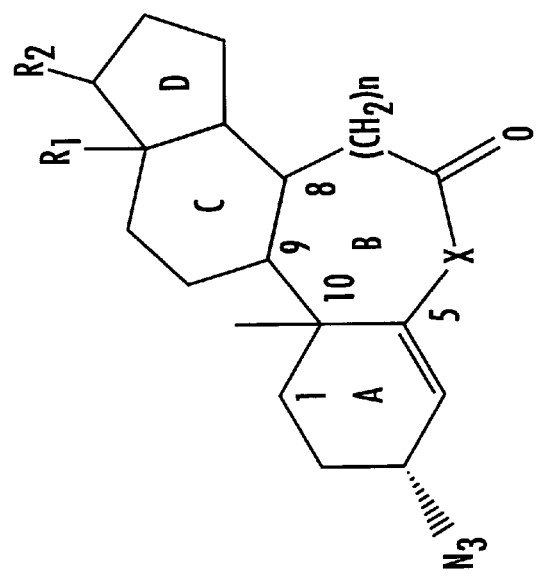
FORMULA (Ia)
FIG. 1

SCHEME 3 OPTIONAL HYDROGENATION OF THE PYROLYSIS PRODUCTS

FIG. 4 SCHEME 4 BASE CATALYZED HYDROLYSIS AND INTRAMOLECULAR MICHAEL ADDITION OF COMPOUNDS 6 AND 15

SCHEME 5    SYNTHESIS OF THE PYROLYSIS PRECURSOR 3-α-AZIDO-B-HOMO-6-OXA-4-CHOLESTEN-7-ONE (a) O $O_3$, -60° C, HEXANE, 45 MIN; PIPERIDINE, 0° C, 3HR; 2M HCl; (b) $SOCl_2$, $CH_2Cl_2$, 2HR; (c) 2 EQUIV. $NaN_3/H_2O$(10%), ACETONE, 2HR.

6,011,058

SECO-CHOLESTANE DERIVATIVES AND METHODS OF MAKING THE SAME

The present invention was made with Government support under Grant No. CA52995 from the National Institutes of Health. The Government has certain rights to this invention.

FIELD OF THE INVENTION

The present invention relates to novel seco-cholestane derivatives and methods of making the same. More particularly, the invention relates to ring-opened, C5- and C8-substituted seco-cholestane derivatives having CDC25 phosphatase inhibition properties and anti-tumor activities.

BACKGROUND OF THE INVENTION

The survival and functioning of cells relies on the elaborate intercellular and intracellular communication network known as signal transduction pathways. These pathways coordinate proliferation, differentiation, metabolism, cell adhesion and motility, protein sorting and transportation of multitudes of cells in different tissues and organs. The malfunctions of these pathways can result in many diseases such as cancer and rheumatoid arthritis. Therefore, great effort has been focused on the development of therapies based on blocking cellular signaling in the diseased cells. Levitzki, A., *Targeting signal transduction for disease therapy,* Current Opinion in Cell Biology, 1996, 8, 239–244.

Intracellular signaling is a series of coupled events that transduce stimuli from outside of the cell into the cell. The signals are relayed by different sets of signal transducer proteins in a sequential fashion, and result in cellular responses. In this process, post-translational modifications of proteins by addition and removal of phosphate groups provide molecular switches to turn on and turn off the function of various transducer proteins. A broad family of protein phosphatases catalyzes the removal of phosphate groups from serine, threonine or tyrosine residues on proteins.

CDC25 comprises a family of dual specificity protein phosphatases which act to remove inhibitory phosphates from cdk kinases and activate cyclin dependent kinase complexes that trigger cell cycle progression. Sadhu, K. et al., *Human homolog of fission yeast cdc25 mitotic inducer is predominantly expressed in G2,* Proc. Nat. Acad. Sci. U.S.A. 1990, 87, 5139–5143; Galaktionov, K. and Beach, D., *Specific activation of cdc25 tyrosine phosphatases by B-type cyclins: evidence for multiple roles of mitotic cyclins,* Cell 1991, 67, 1181–1194. In human cells, CDC25 consists of three phase specific isoforms, CDC25A, B and C. CDC25A is expressed early in the $G_1$ phase of the cell cycle, and is essential for transition from $G_1$ to S phase. Jinno, S. et al., *Cdc25A is a novel phosphatase functioning early in the cell cycle,* EMBO J, 1994, 13, 1549–1556.

The activation of at least two cyclin-dependent kinases, required for G1 to S phase progression, depends on the dephosphorylation of the catalytic cdk subunit at Tyr-15 and Thr-14 near the ATP-binding site. The phorsphorylation of these two residues blocks the binding of ATP to the cyclincdk complex and renders the complex catalytically inactive. The dephorsphorylation of both cyclin E-cdk2 and cyclin A-cdk2 complexes by CDC25A is tightly regulated in normal cells. Accumulating evidence suggests that inappropriate amplification or activation of CDC25A is characteristic of a number of cancers, including breast cancer. Galaktionov, K. et al, *CDC25 phosphatases as potential human oncogenes,* Science, 1995, 269, 1575–1577; Gasparotto, D. et al., *Overexpression of CDC25A and CDC25B in head and neck cancers,* Cancer Res, 1997, 57, 2366–2368; Galaktionov, K., et al., *Cdc25 cell-cycle phosphatase as a target of c-myc,* Nature, 1996, 382, 511–517; Hernandez, S. et al., *cdc25 cell cycle-activating phosphatases and c-myc expression in human non-Hodgkin's lymphomas,* Cancer Res 1998, 58(8):1762–1767. Thus increased CDC25A activities may contribute to the dysregulated growth of certain types of tumor cells. Both CDC25A and B phosphatases are considered promising target enzymes for the development of anti-cancer drugs. Draetta, G. and Eckstein, J. W., *Cdc25 protein phosphatases in cell proliferation,* Biochimica et Biophysica Acta, 1997, 1332, M53–M63.

Although CDC25 phosphatases have been identified as playing a crucial role in the replication cycle of cancer cells, studies of the intracellular function of CDC25 phosphatases have been severely hampered by the lack of potent inhibitors. To date few therapeutic agents have been reported as specific targets for these enzymes or as inhibitors of their activity. Vanadate, a broad-spectrum protein phosphatase inhibitor was the first CDC25A inhibitor found. Baratte B. et al., *Screening for antimitotic compounds using the cdc25 tyrosine phosphatase, an activator of the mitosis-inducing p34cdc2/cyclin Bcdc13 protein kinase,* Anticancer Res 1992, 12(3):873–880. In 1996, the natural product dysidiolide was reported as a cdc25A inhibitor with an $IC_{50}$ value of 9.4 $\mu$M. Gunasekera, S. P. et al., *Dysidiolide: A Novel Protein Phosphatase inhibitor from the Caribbean Sponge Dysidea ehteria de Laubenfels,* J.Am.Chem.Soc. 1996, 118, 8759–8760. Later, Rice and coworker also synthesized a group of inhibitors based on the pharmacophore of protein tyrosine phosphatase (PTPase) inhibitors. Rice, R. L. et al., *A targeted Library of Small-Molecule, Tyrosine, and Dual-Specificity Phosphatase Inhibitors Derived from a Rational Core Design and Random Side Chain Variation,* Biochemistry, 1997, 36, 15965–15974. This series of compounds inhibited CDC25A phosphatase competitively, the most potent inhibitor having an $IC_{50}$ value of 15 $\mu$M.

As discussed above, the dual specificity protein phosphatase (CDC25A) plays a crucial role in cancer cell proliferation, and there exists a need for efficient synthetic routes for more potent CDC25A inhibitors. However, the total synthesis of natural products is usually lengthy, and with lower yields. Readily available natural products, with defined stereochemistry and useful functional groups, can be utilized with novel and efficient chemical transformations to solve the difficult problems. The pyrolysis of alkyl azides to form cyano groups has been reported. Bock, H. and Dammel, R., *Gas-Phase Pyrolysis of Alkyl Azide: Experimental Evidence for Chemical Activation,* J.Am.Chem.Soc. 1988, 110, 5261–5269. However, no report has appeared on the pyrolysis of azido-steroids on the surface of silica gel.

SUMMARY OF THE INVENTION

The present invention relates to the discovery of a group of novel seco-cholestane derivatives possessing pharmaceutical activities, including CDC25 phosphatase inhibition properties, and tumor cell growth inhibition activities. The present invention also relates to the discovery of an efficient synthetic route to C5- and C8- substituted seco-cholestane derivatives of Formula (I), by pyrolyzing readily available azido-cholestane precursors with the option of introducing functionality as needed.

A first aspect of the present invention is directed to C5- and C8-substituted seco-cholestane derivatives of the Formula (I)

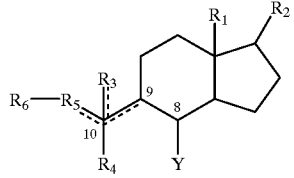

wherein:

$R_1$ is selected from the group consisting of H, lower alkyl, and alkoxy;

$R_2$ is selected from the group consisting of C1–C10 alkyl, substituted C1–C10 alkyl, C2–C10 alkene containing one to four double bonds, substituted C2–C10 alkene, and C1–C10 alkyl or C2–C10 alkene having one or more heteroatoms selected from the group consisting of oxygen atoms and nitrogen atoms inserted into the chain thereof, the chain having 10 or less atoms including the hetero atoms;

$R_3$ is selected from the group consisting of methylene, ketone, and methyl;

$R_4$ is absent when $R_3$ is methylene or ketone, or when $R_3$ is methyl, $R_4$ is selected from the group consisting of hydrogen, lower alkyl, alkoxy, lower alkanoyloxy, hydroxy, carboxyl, amino, lower alkylamino, and halo, or $R_4$ is an oxygen atom and together with the C10 atom to which $R_4$ is attached and $R_5$ comprises a heterocyclic ring and the double bond between C10 and $R_3$, C9 and C10, or C10 and $R_5$ is absent;

Y is C1–C6 alkyl or C2–C6 alkene terminating in an amide group —CONH$_2$, a nitrile group —CN, or an acid group, including, but not limited to, a carboxylic acid group CO$_2$H, a sulfonic acid group SO$_3$H, a carbodithioic acid group —CSSH, or a phosphoric acid group PO(OH)$_2$, or salts of these acidic groups, or Y is —(CH$_2$)$_n$—C(O)—X—, wherein n is an integer from 1 to 3, X is oxygen or nitrogen, and together with C8 atom to which Y is attached, the C9 atom, and the C10 atom constitute a ring system comprising a 6 to 8 membered lactone or lactam ring, or Y is —(CH$_2$)—C(O)—O—, and together with the C8 atom to which Y is attached, the C9 atom, the C10 atom, and $R_5$ constitute a ring system comprising a lactone ring when $R_3$ is methyl, $R_4$ is hydroxyl and the double bond between C10 and $R_3$, $R_5$ and C10 or C9 and C10 is absent;

$R_5$ is selected from the group consisting of C2–C8 alkyl, C2–C8 alkene having one or more double bonds, substituted C2–C8 alkyl, and substituted C2–C8 alkene;

$R_6$ is a functional group selected from the group consisting of CN, COOH, CSSH, or salts of these acid groups, CHO, CH$_2$OH, CONH$_2$, and CONR$_2$, wherein R is lower alkyl, acyl or H, and optionally a hydrogen atom of a carbon atom adjacent $R_6$ may be replaced with identical functional groups described above; and the broken lines indicate optional double bonds, and pharmaceutically acceptable salts of the compounds of Formula (I).

In one preferred embodiment of the invention, the compounds of the invention have the formula (Ia):

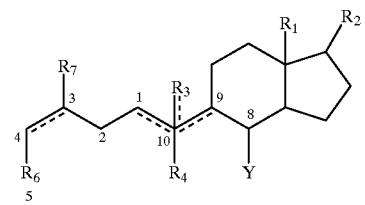

wherein:

$R_1$, $R_2$, $R_3$, $R_4$, $R_6$, and Y are the same as defined above, and $R_7$ is a substituent introduced by Michael Addition of nucleophiles to the double bond between C3 and C4 when present, such as, but not limited to hydroxy, lower alkoxy, e.g., methoxy, lower alkanoyloxy, e.g., acetoxy, amino, lower alkyl amino, e.g. methyl amino, carboxyl, acetylene, cyano, lower alkyl, lower alkene, cycloalkyl, e.g., cyclopropyl, and the like. In this embodiment of the invention, $R_5$ is C4 alkyl or C4 alkene having one or more double bonds as indicated by the dotted lines. Further, in this embodiment of the invention, Y can be —(CH$_2$)—C(O)—O— and together with the C8 atom to which Y is attached, C9, C10, C1, C2 and C3 atoms, constitute a nine membered lactone ring. Still further, in this embodiment of the invention, $R_4$ can be oxygen and together with C3 and C10 to which it is attached, and C1 and C2, constitute a five membered tetrahydrofuran ring.

Another aspect of the present invention includes methods for synthesizing the seco-cholestane derivatives of Formula (I). In this aspect of the invention, 3-α-azido-B-homo-6-oxa-4-cholesten-7-one is heated under conditions sufficient to open rings A and B thereof and to provide a chain containing a conjugated cyano group, while leaving the cholesteryl C and D rings and the side chain intact. The method further includes optional hydrogenation or hydrolysis/Michael Addition steps.

The invention also provides pharmaceutical compositions comprising the seco-cholestane derivatives of Formula (I) and one or more pharmaceutically acceptable carriers or diluents.

BRIEF DESCRIPTION OF THE DRAWINGS

In the drawings which form a portion of the disclosure of the invention:

FIG. 1 illustrates a general reaction Scheme 1 for preparing the compounds of Formula (I);

DETAILED DESCRIPTION OF THE INVENTION

Figure 2:
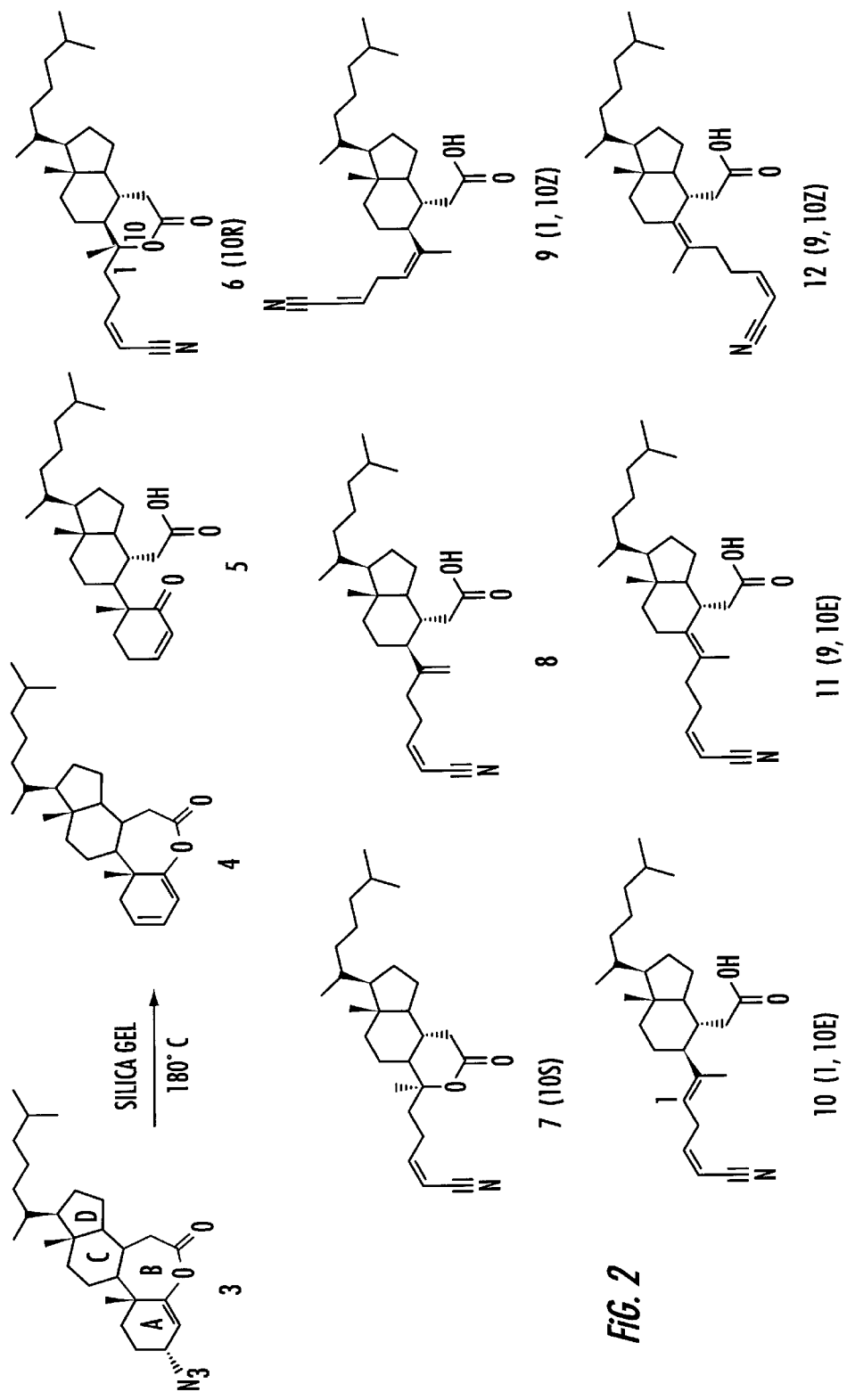
FIG. 2 illustrates one embodiment of the invention, namely, Scheme 2 illustrating the pyrolysis of the precursor 3α-azido-B-homo-6-oxa-4-cholesten-7-one on silica gel.
Figure 3:
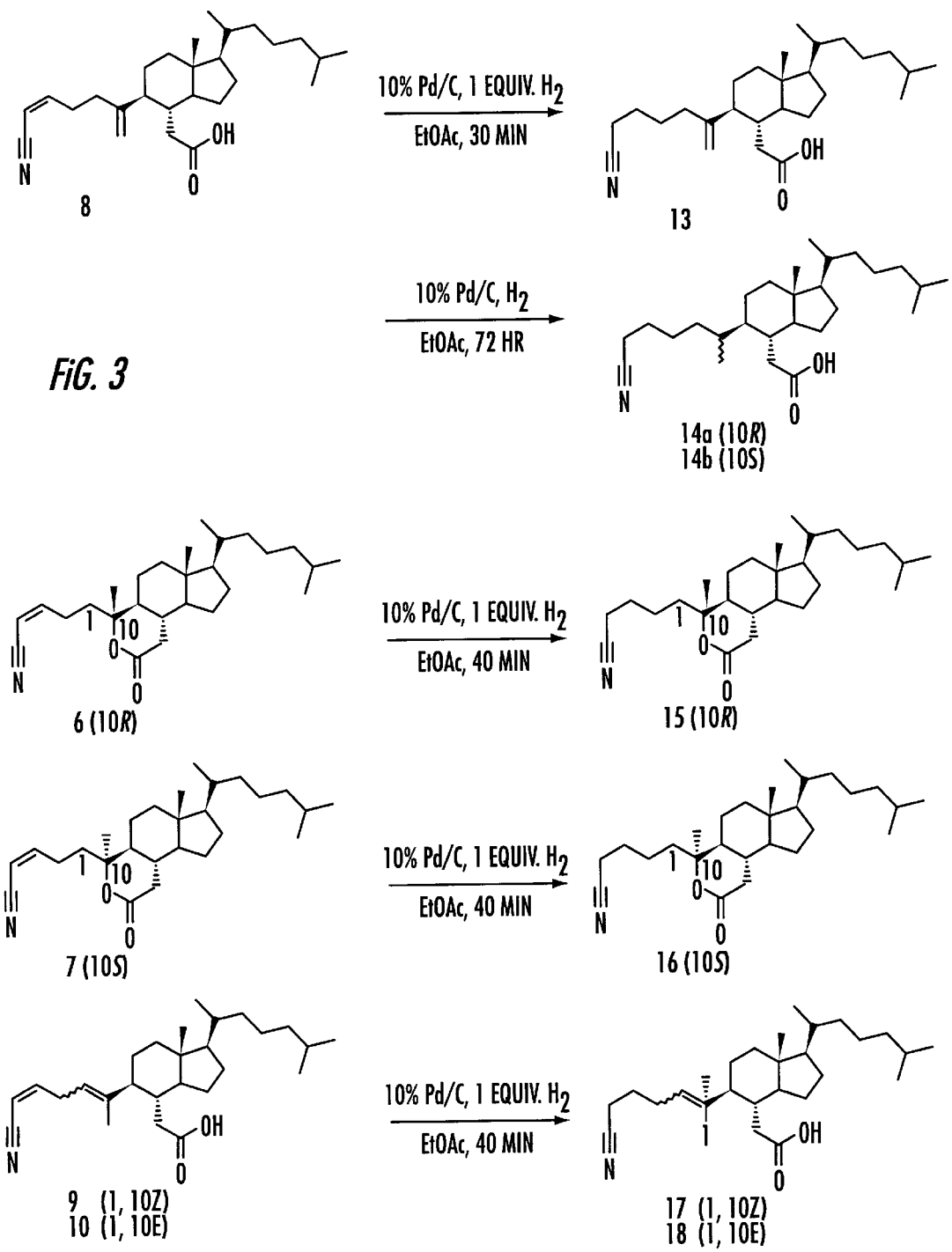
FIG. 3 illustrates the optional hydrogenation of the pyrolysis products of FIG. 2.
Figure 4:
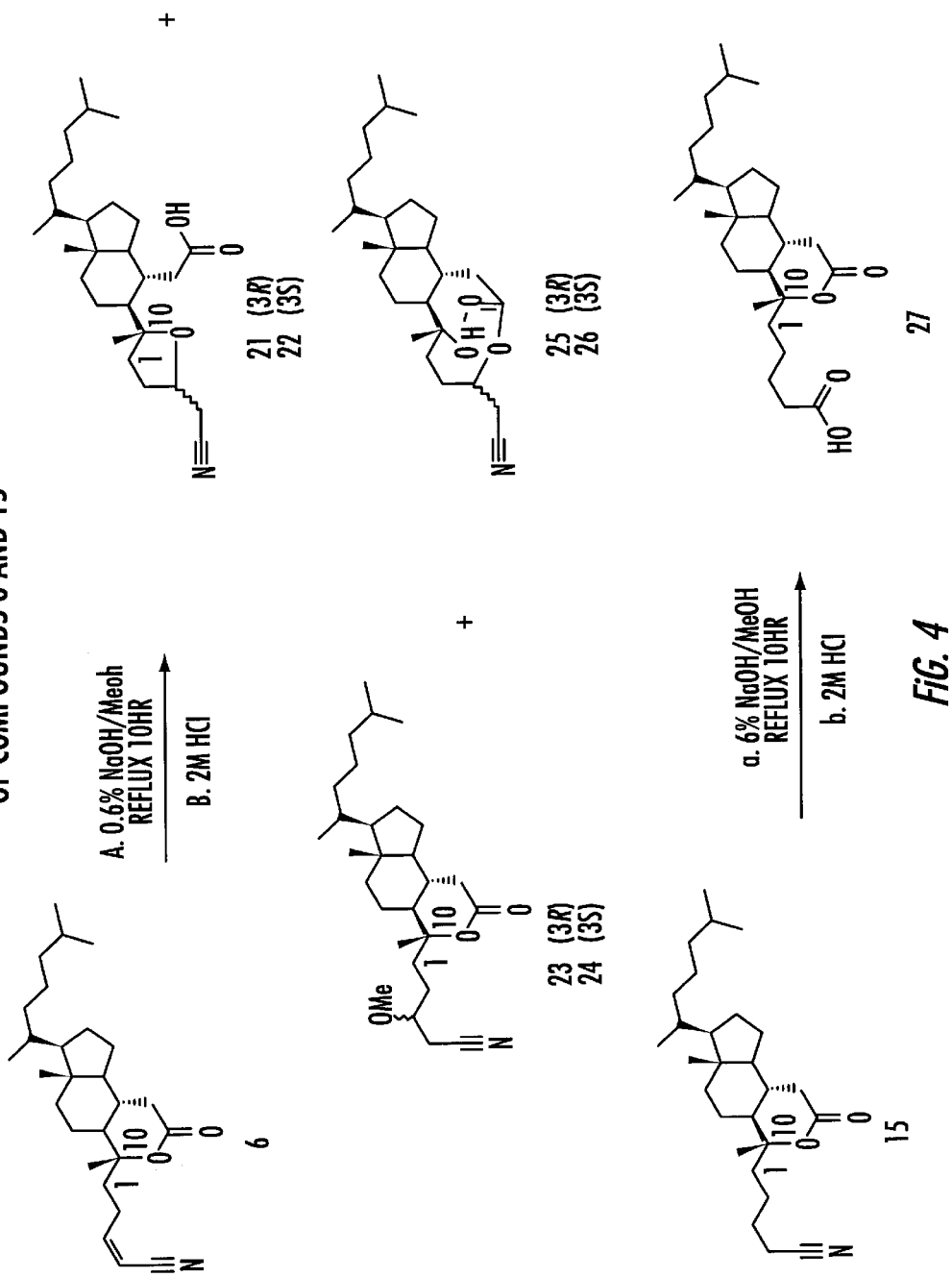
FIG. 4 illustrates the optional steps of base catalyzed hydrolysis and intramolecular Michael addition of the pyrolysis products of FIG. 2 and the hydrogenation products of FIG. 3.

The present invention is directed to compounds of Formula (I)

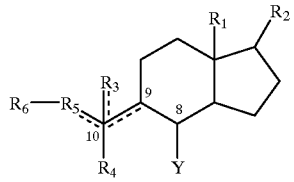

wherein:

$R_1$ is selected from the group consisting of H, lower alkyl, and alkoxy;

$R_2$ is selected from the group consisting of C1–C10 alkyl, substituted C1–C10 alkyl, C2–C10 alkene containing one to four double bonds, substituted C2–C10 alkene, and C1–C10 alkyl or C2–C10 alkene having one or more heteroatoms selected from the group consisting of oxygen atoms and nitrogen atoms inserted into the chain thereof, the chain having 10 or less atoms including the hetero atoms;

$R_3$ is selected from the group consisting of methylene, ketone, and methyl;

$R_4$ is absent when $R_3$ is methylene or ketone, or when $R_3$ is methyl, $R_4$ is selected from the group consisting of hydrogen, lower alkyl, alkoxy, lower alkanoyloxy, hydroxy, carboxyl, amino, lower alkylamino, and halo, or $R_4$ is an oxygen atom and together with the C10 atom to which $R_4$ is attached and $R_5$ comprises a heterocyclic ring and the double bond between C10 and $R_3$, C9 and C10, or C10 and $R_5$ is absent;

Y is selected from the group consisting of C1–C6 alkyl or C2–C6 alkene terminating in an amide group —$CONH_2$, a nitrile group —CN, or an acid group(s), including, but not limited to carboxylic acid group $CO_2H$, sulfonic acid group $SO_3H$, carbodithioic acid group CSSH, or phosphoric acid group $PO(OH)_2$, or salts of these acidic groups, or Y is —$(CH_2)_n$—C(O)—X—, wherein n is an integer from 1 to 3, X is oxygen or nitrogen, and together with C8 atom to which Y is attached, the C9 atom, and the C10 atom constitute a ring system comprising a 6 to 8 membered lactone or lactam ring, or Y is —$(CH_2)$—C(O)—O—, and together with the C8 atom to which Y is attached, the C9 atom, the C10 atom, and $R_5$ constitute a ring system comprising a lactone ring when $R_3$ is methyl, $R_4$ is hydroxyl and the double bond between C10 and $R_3$, $R_5$ and C10 or C9 and C10 is absent;

$R_5$ is selected from the group consisting of C2–C8 alkyl, C2–C8 alkene having one or more double bonds, substituted C2–C8 alkyl, and substituted C2–C8 alkene;

$R_6$ is a functional group selected from the group consisting of CN, COOH, CSSH, or salts of these acid groups, CHO, $CH_2OH$, $CONH_2$, and $CONR_2$, wherein R is lower alkyl, acyl or H, and optionally a hydrogen atom of a carbon atom adjacent $R_6$ may be replaced with identical functional groups described above; and the broken lines indicate optional double bonds, and pharmaceutically acceptable salts of the compounds of Formula (I).

As used herein, the term "compound" is intended to refer to a chemical entity, whether in the solid, liquid or gaseous phase, and whether in a crude mixture or purified and isolated. The terms "alkyl," "alkene," and "alkoxy" include straight chain and branched alkyl, alkene, and alkoxy, respectively. The term "lower alkyl" refers to C1–C4 alkyl. The term "alkoxy" refers to oxygen substituted alkyl, for example, of the formulas —OR or —ROR', wherein R and R' are each independently selected from lower alkyl and wherein the alkoxy group includes four or fewer atoms in the chain, including the oxygen atom. The terms "substituted alkyl" and "substituted alkene" refer to alkyl and alkene, respectively, substituted with one or more simple substitutents, such as but not limited to, C3–C6 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like. The term "lower alkanoyloxy" refers to C1–C4 alkanoyloxy. The term "lower alkylamino" refers to C1–C4 alkylamino. The term "substituted phenyl" refers to phenyl substituted with one or more simple substitutents, such as but not limited to lower alkyl, hydroxy, carboxyl, halo, sulfato, sulfonyloxy, amino, alkoxy, and the like.

In one preferred embodiment of the invention, the compounds have the formula (Ia):

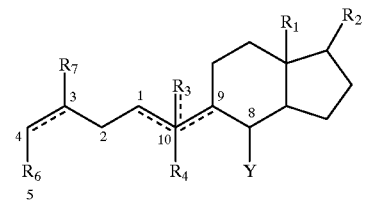

wherein:

$R_1$, $R_2$, $R_3$, $R_4$, $R_6$, and Y are the same as defined above, and $R_7$ is a substituent introduced by Michael Addition of nucleophiles to the double bond between C3 and C4 when present, such as, but not limited to hydroxy, lower alkoxy, e.g., methoxy, lower alkanoyloxy, e.g., acetoxy, amino, lower alkyl amino, e.g. methyl amino, carboxyl, acetylene, cyano, lower alkyl, lower alkene, cycloalkyl, e.g., cyclopropyl, and the like. In this embodiment of the invention, $R_5$ is C4 alkyl or C4 alkene having one or more double bonds as indicated by the dotted lines. Further, in this embodiment of the invention, Y can be —$(CH_2)$—C(O)—O— and together with the C8 atom to which Y is attached, C9, C10, C1, C2 and C3 atoms, constitute a nine membered lactone ring. Still further, in this embodiment of the invention, $R_4$ can be oxygen and together with C3 and C10 to which it is attached, and C1 and C2, constitute a five membered tetrahydrofuran ring.

In this embodiment of the invention, the compounds of Formula (Ia) include those compounds wherein $R_1$ is methyl, $R_2$ is —$CH(CH_3)$ $(CH_2)_3CH(CH_3)_2$, Y is —$CH_2$—C(O)—OH, and $R_6$ is CN. In one aspect of this embodiment of this invention, the compounds of Formula (Ia) include those compounds wherein $R_3$ is —$CH_3$, the double bonds are absent between $R_3$ and C10, C1 and C10, C9 and C10, the double bond is also absent between C3 and C4, $R_7$ is hydrogen, and $R_4$ is an oxygen atom and together with C3 and C10 to which it attached, and C1 and C2, constitute a 5 membered tetrahydrofuran ring. The compounds of this aspect of this embodiment of the invention include compounds in either an R configuration or an S configuration at C10. In another aspect of this embodiment of the invention, the compounds of Formula (Ia) include those compounds wherein $R_3$ is =$CH_2$ and the double bond is present between C10 and $R_3$, the double bond is absent between C1 and C10, the double bond is absent between C9 and C10, and the double bond is present between C3 and C4 with a Z configuration. In another aspect of this embodiment of the invention, the compounds of Formula (Ia) include those compounds wherein $R_3$ is —$CH_3$, $R_4$ is —H, and the double bond is absent between C10 and $R_3$, the double bond is absent between C9 and C10, the double bond is present between C1 and C10, and the double bond is present between C3 and C4 with a Z configuration. This embodiment of the invention includes those compounds in either a Z configuration or an E configuration between C1 and C10. In yet another aspect of this embodiment of the invention, the compounds of Formula (Ia) include those compounds wherein $R_3$ is —$CH_3$ and the double bond is absent between C10 and $R_3$, the double bond is absent between C1 and C10, the double bond is present between C10 and C9, and the double bond is present between C3 and C4 with a Z configuration. This embodiment of the invention includes those compounds in either a Z or E configuration between C9 and C10. In yet another aspect of this embodiment of the invention, the compounds of Formula (Ia) include those compounds wherein $R_3$ is =$CH_2$ and the double bond is present between C10 and $R_3$, the double bond is absent between C1 and C10, the double bond is absent between C9 and C10, and the double bond is absent between C3 and C4. In yet another aspect of this embodiment of the invention, the compounds of Formula (Ia) include those compounds wherein $R_3$ is —$CH_3$, and the double bond is absent between C10 and $R_3$, the double bond is absent between C10 and C9, the double bond is present between C1 and C10, and the double bond is absent between C3 and C4. This embodiment of the invention includes those compounds in either a Z or E configuration between C1 and C10. In yet another aspect of this embodiment of the invention, the compounds of Formula (Ia) include those compounds wherein $R_3$ is —$CH_3$ and the double bond is absent between C10 and $R_3$, the double bond is absent between C1 and C10, the double bond is present between C10 and C9, and the double bond is absent between C3 and C4. This embodiment of the invention includes those compounds in either a Z or E configuration between C9 and C10. In yet another aspect of this embodiment of the invention, the compounds of Formula (Ia) include those compounds wherein $R_3$ is —$CH_3$, $R_4$ is —H, the double bond is absent between C9 and C10, and the double bond is absent between C10 and $R_3$, the double bond is absent between C1 and C10, and the double bond is absent between C3 and C4. This aspect of this embodiment of the invention includes those compounds in either an R configuration or an S configuration of 19-Me at C10.

In another embodiment of the invention, the compounds of Formula (Ia) are those compounds wherein $R_1$ is methyl, $R_2$ is —CH($CH_3$) ($CH_2$)$_3$ CH($CH_3$)$_2$, $R_6$ is CN, Y is —$CH_2$—C(O)—O— and together with the C8 atom to which Y is attached, the C9, and the C10 atoms constitute a ring system comprising a 6 membered lactone ring. In one aspect of this embodiment of the invention, the compounds include those compounds wherein $R_3$ is —$CH_3$ and the double bond is absent between C10 and $R_3$, the double bond is absent between C9 and C10, the double bond is absent between C1 and C10 and the double bond is present between C3 and C4 with a Z configuration. In another aspect of this embodiment of the invention, the compounds include those compounds wherein $R_3$ is —$CH_3$ and the double bond is absent between C10 and $R_3$, the double bond is absent between C1 and C10, the double bond is absent between C9 and C10, and the double bond is absent between C3 and C4. In another aspect of this embodiment of the invention, the compounds of Formula (Ia) include those compounds wherein $R_3$ is —$CH_3$, the double bonds are absent between $R_3$ and C10, C1 and C10, and C9 and C10, the double bond is absent between C3 and C4, $R_7$ is —OMe with either an R configuration or an S configuration. The compounds of this embodiment of the invention include those compounds in either an R configuration or an S configuration at C10.

In another embodiment of the invention, the compounds of formula (Ia) are those compounds wherein $R_1$ is methyl, $R_2$ is —CH($CH_3$) ($CH_2$)$_3$CH($CH_3$)$_2$, $R_6$ is —CN, $R_4$ is —OH, and Y is —$CH_2$—C(O)—X, wherein X is an oxygen atom, and together with the C8 atom to which Y is attached, the C9, C10, C1, C2 atoms, and the C3 atom to which X is attached, constitute a 9 membered lactone ring. This embodiment of the invention includes those compounds in either an R configuration or an S configuration at C10.

Examples of compounds exemplary of Formula (I) above include, but are not limited to:

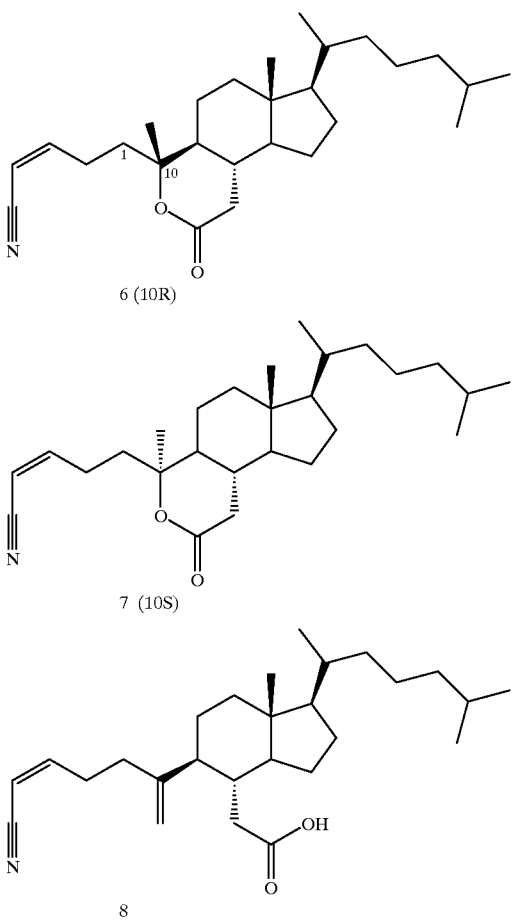

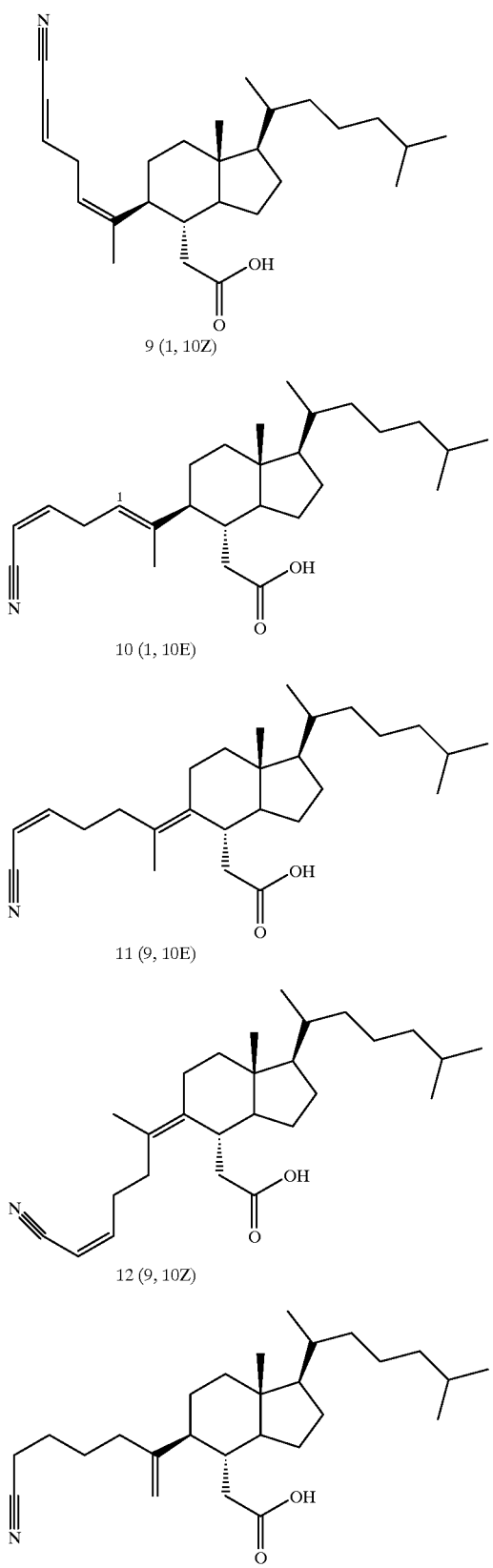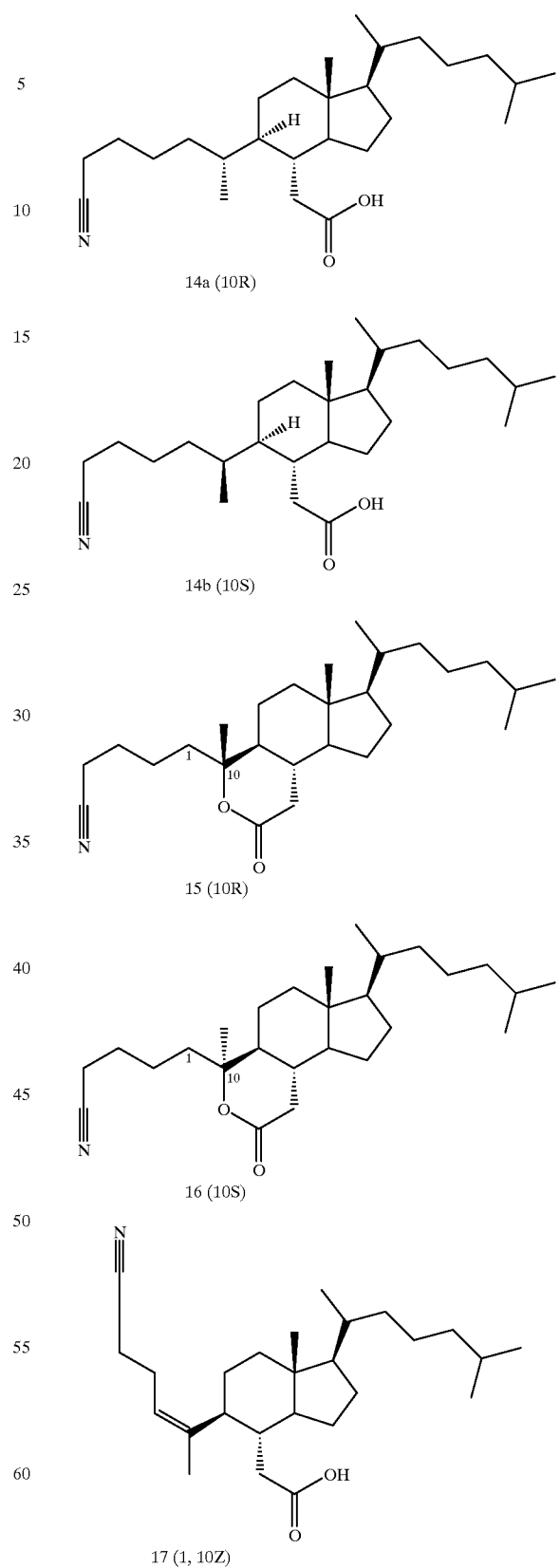

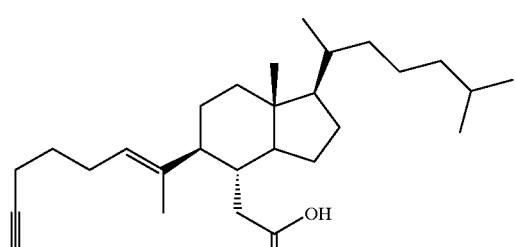
18 (1, 10E)
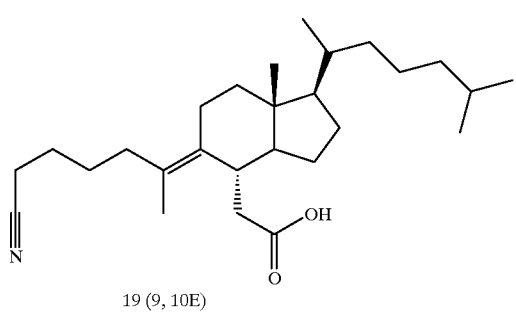
19 (9, 10E)
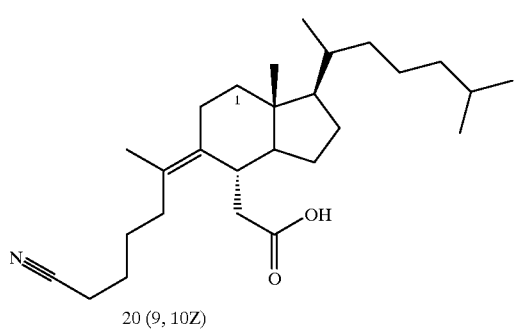
20 (9, 10Z)
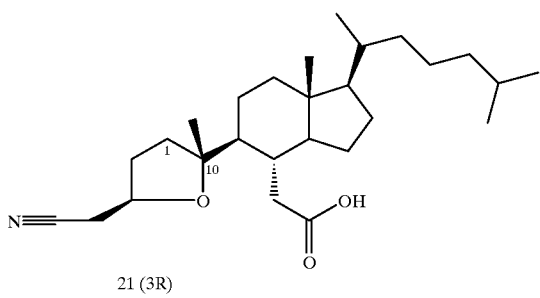
21 (3R)
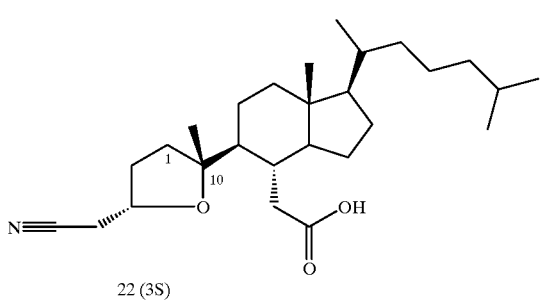
22 (3S)
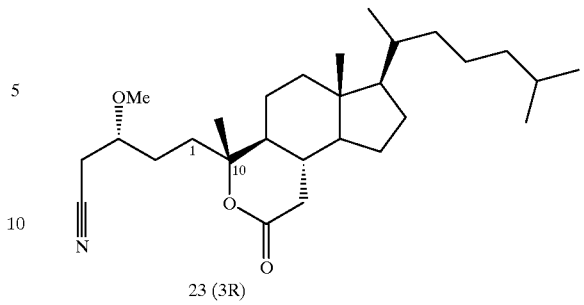
23 (3R)
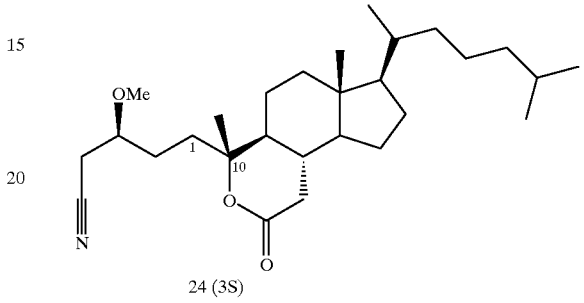
24 (3S)
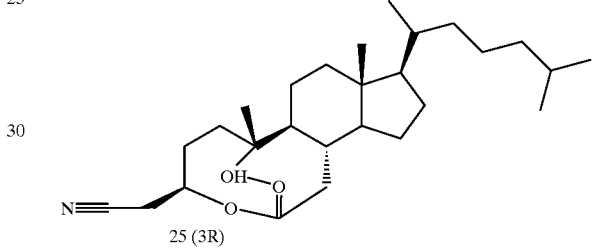
25 (3R)
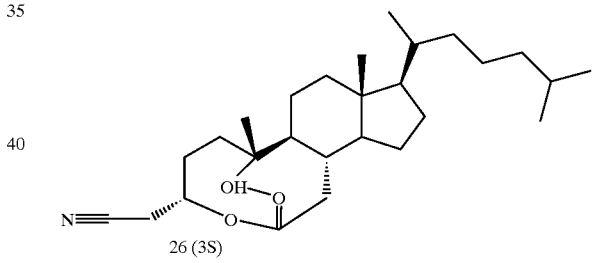
26 (3S)
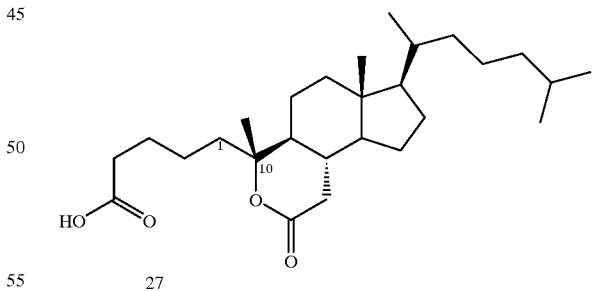
27
and the like and pharmaceutically acceptable salts thereof.
Illustrative examples of the synthesis of C5- and C8-substituted seco-cholestane derivatives of Formula (I) according to the present invention are given in Scheme 1 of FIG. 1, and in Schemes 2, 3, 4, and 5 of FIGS. 2, 3, 4, and 5, respectively, with more detail.

Referring to FIG. 1 and Scheme 1, generally the compounds of invention can be prepared by pyrolysis of compound 3 (wherein $R_1$ and $R_2$ have the meanings ascribed above, n is an integer from 1 to 3, and X is oxygen or nitrogen) under conditions sufficient to open rings A and B to give a side chain containing a cyano group, while leaving the cholesteryl C and D rings and side chain ($R_2$) intact. $R_1$, $R_2$, $R_3$, $R_4$ and Y of the reaction product have the meanings ascribed above. Preferably, the pyrolysis reaction is conducted on a suitable solid support, such as a conventional silica gel as known in the art, at a temperature ranging from about 100° C. to about 250° C., and more preferably at a temperature of about 180° C.

Referring still the FIG. 1, the resultant reaction product can be subjected to additional chemistries as known in the art to provide compounds of Formula (I). For example, the chain length of the alkyl or alkene chain between C10 and CN can be modified to provide a C2–C8, substituted or unsubstituted, alkyl or alkene chain using reactants and processes as known in the art. See "Comprehensive Organic Transformations," Richard C. Larock, VCH Publishers, Inc., New York, N.Y., 1989; "Comprehensive Organic Chemistry," edited by C. J. Drayton. Sir Derek Barton, F. R. S. and W. David Ollis, F. R. S., Perganon Press, 1979, Volumes 1–6; "The Organic Chemistry of Drug Synthesis," by Daniel Lednier et al., John Wiley & Sons, Inc., 1995, Vols. 1–5. In addition, the functionality of the nitrile group can also be modified using conventional functionalizing agents known in the art and known procedures to provide the functionalities as described above with regard to the definition of $R_6$. Further, when Y includes a carboxylic acid group, the functionality of the carboxylic acid group can also be modified using conventional reagents and processes, for example, to provide amide, nitrile sulfonic acid groups, carbodithioic acid groups, phosphoric acid groups or salts thereof. See above references.

The resultant reaction product typically includes a mixture of compounds such as illustrated in Scheme 2 of FIG. 2. FIG. 2 illustrates one preferred embodiment of the invention in which compound 3 is 3-α-azido-B-homo-6-oxa-4-cholesten-7-one (wherein n is 1 and X is oxygen). The compounds can be isolated using conventional purification techniques, such as flash chromatography and preparative thin layer chromatography, or HPLC techniques.

The compounds produced in accordance with Scheme 2 can be subjected to an optional hydrogenation step to saturate at least one of the double bonds, for example, present in the cyano containing side chain and/or at C1. Exemplary hydrogenation reactions are illustrated in Scheme 3 of FIG. 3.

The compounds produced in accordance with Scheme 2 can also optionally be subjected to base catalyzed hydrolysis or solvolysis to convert $R_6$ from —CN to —COOH or —CONH$_2$. Functional groups can also be introduced at C3 through the Michael Addition of any nucleophiles to the conjugated double bond between C3 and C4. Further, the lactone ring in compounds 6, 7, 15 and 16 can be hydrolyzed, into —COOH and —OH, which can in turn undergo intramolecular Michael additions to the C3 double bond to form a 9 membered lactone ring or 5 membered tetrahydrofuran ring, respectively. Exemplary base catalysed hydrolysis and intramolecular Michael Addition reactions are illustrated in Scheme 4 of FIG. 4.

Figure 5:
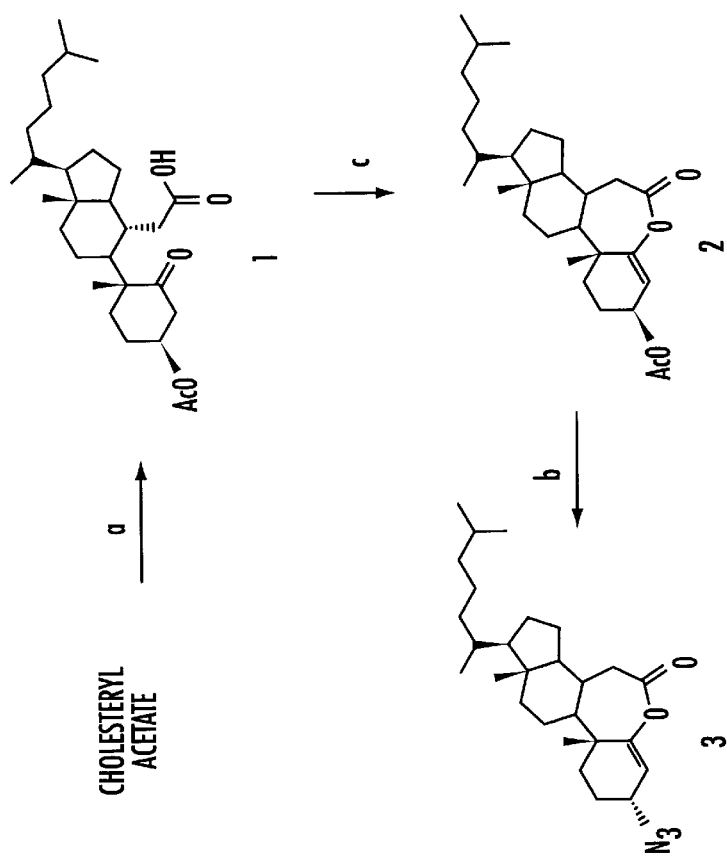
FIG. 5 illustrates the synthesis of the pyrolysis precursors 3α-azido-B-homo-6-oxa-4-cholesten-7-one of FIG. 2.

The starting reactant 3 can be readily prepared from cholesteryl acetate or derivatives thereof as illustrated in Scheme 5 of FIG. 5. Cholesteryl acetate and derivatives thereof (i.e., in which n is 2 or 3 and/or X is nitrogen) are commercially available or can be produced using known techniques (see references above).

For example, referring to Scheme 5 of FIG. 5, compound 3 can be prepared by ozonolysis of cholesteryl acetate (Lettre, H., Mathes, K., Wagner, M., Liebigs Ann. Chem., 1967, 703, 147–151) under conditions sufficient to form the keto acid thereof (Compound 1). The keto acid 1 is then subjected to a ring closure step and converted to the lactone 3β-actoxy-B-homo-6-oxa-4-cholesten-7-one (2). Compound 2 is then exposed to sodium azide at room temperature to produce 3-α-azido-B-homo-6-oxa-4-cholsten-7-one (3), which can be further used as discussed above to produce the compounds of the invention.

An alternative way to synthesize the compounds in this invention is to use 5,6-seco-5-oxo-3, 4-choleten-6-oic acid, which could be readily produced from cholesteryl acetate, as a starting material. After protection of the carboxlic acid group with $CH_2N_2$, the compound can be converted to an oxime, which in the presence of Lewis acid, e.g. $PCl_3$, can undergo Beckmann fragmentation reaction (Rodewald, W. J., Zaworska, A, Polish J. of Chem, 1980, 54 1147–1155; Rodewald, W. J., Achmatowicz, B., Roczniki Chemii, 1972, 46, 203–208) to produce compounds 8 to 12. Another alternative way to synthesize the compounds in this invention is to use Schmidt fragmentation reaction (Barton D., and Ollis W. D. et al. Comprehensive Organic Chemistry, the Synthesis and Reaction of Organic Compounds, Pergamon Press, 1979, volume 2, 968–970. Sunaramaiah, A. et al. J. Indian Chem. Soc. 1976, LIII, 664) of 5,6-seco-5-oxo-3, 4-choleten-6-oic acid to produce compounds 8 to 12.

The compounds of Formula (I) can have pharmaceutical activity and can be useful in the treatment of a subject suffering from one or more maladies. Subjects which can be treated include animal subjects, typically vertebrates, including both mammalian (e.g., human, cat, dog, cow, horse, sheep, pig, monkey, ape, etc.) and avian subjects (e.g., chicken, turkey, duck, goose, quail, pheasant, etc.). It is believed, for example, that administering the compounds of Formula (I) to a subject can result in inhibition of cdc25 phosphatase activity, and further that such compounds can be useful as cancer therapeutic agents. Moreover, because of the specificity of the targeting, use of the compounds of Formula (I) could possibly reduce some of the deleterious side effects that often accompany the use of conventional chemotherapeutic agents. Thus the present invention can provide methods for treating tumor-bearing subjects in which the compounds of the invention are administered to the subject in need of such treatment in an amount effective and in a manner effective to combat such tumors, for example, by virtue of targeting cdc25 phosphatase activity in the cancer cells.

The compounds of Formula (I) may be administered per se or in the form of a pharmaceutically acceptable salt. When used in medicine, the salts of the compounds of Formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Pharmaceutically acceptable salts can be prepared as alkaline metal or alkaline earth salts, such as sodium, potassium, or calcium salts of the carboxylic acid group. Thus the present invention also provides pharmaceutical formulations or compositions, both for veterinary and for human medical use, which comprise the compounds of formula (I) or a pharmaceutically acceptable salt thereof with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

The salts of the present invention may be prepared, in general, by reacting a compound of the invention with the desired base in solution. After the reaction is complete, the salts can be crystallized from solution by the addition of an appropriate amount of solvent in which the salt is insoluble.

The compositions includes those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier or both, and then, if necessary, shaping the product into desired formulations.

Compositions of the present invention suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parental administration conveniently comprise a sterile aqueous preparation of the active compound, which can be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

In addition to the aforementioned ingredients, the compositions of the invention may further include one or more accessory ingredient(s) selected from the group consisting of diluents, buffers, flavoring agents, binders, disintegrants, surface active agents, thickeners, lubricants, preservatives (including antioxidants) and the like.

The therapeutically effective dosage of any specific compound, the use of which is in the scope of the present invention, will vary somewhat from compound to compound, patient to patient, and will depend upon the condition of the patient and the route of delivery. As a general proposition, a dosage from about 2.5 to about 250 mg/kg body weight, preferably from about 10 to about 100 mg/kg, will have therapeutic efficacy. When administered conjointly with other pharmaceutically active agents, even less of the compounds of formula (I) may be therapeutically effective. The compound of Formula (I) may be administered once or several times a day. The duration of the treatment may be once per day for a period of from two to three weeks and may continue for period of months or even years. The daily dose can be administered either by a single dose in the form of an individual dosage unit or several smaller dosage units or by multiple administration of subdivided dosages at certain intervals.

The present invention will be further illustrated by the following non-limiting examples, in which "g" means grams, "mg" means milligrams, "mmol" means millimoles, "ml" means milliliters, "min." means minutes, "hrs" means hours, "HCl" means hydrochloric acid, "M" means molar, "mM" means millimolar, "cm" means centimeters, "mp" means melting point, "°C." means degrees Celsius, and "$\mu$m" means micrometers.

For the following examples, the starting material cholesteryl acetate was purchased from Aldrich. Thin layer chromatography analysis was performed on aluminum sheets precoated with 0.2 mm of silica gel containing 6OF254 indicator. Flash chromatography was run using 230–400 mesh or 10 micron silica gel. Preparative thin layer chromatography was run on Whatman silica gel PK5F 150 Å glass-coated plates with flourescent indicator, bands were visualized by UV light at 254 nm. Proton NMR were recorded on 300 MHz spectrometer; $^{13}$C NMR and DEPT were recorded on 100 MHz spectrometer; the homonuclear $^1$H—$^1$H and heteronuclear $^1$H-$^{13}$C chemical shift correlated 2D diagrams were obtained using the standard COSY 90 and HMQC pulse sequence, respectively, on 500 MHz spectrometer. Two-dimensional nuclear overhauser spectroscopy (NOESY) was also recorded on 500 MHz spectrometer. High resolution mass spectra were obtained by EI or CI.

HT-29 human colon cancer cells and A549 human lung adenocarcinoma cells were purchased from the American Tissue Type Collection (Rockville, Md.). The cell were maintained in Dulbecco's modified Eagle's media (DMEM) containing 10% fetal bovine serum and harvested with 0.05% trypsin and 0.5 mM EDTA before becoming confluent.

In the Examples below, the compound designations have the meanings ascribed above.

EXAMPLE 1

Synthesis of Pyrolysis Precursor
Synthesis of 3-$\beta$-Acetoxy-5, 6-seco-5-oxocholestan-6-oic acid (1)

Ozone was passed into a stirred and cooled (chloroform/dry ice bath) solution of cholesteryl acetate (12 g, 28 mmol) in 300 ml petroleum ether for 30 min until the solution turned into baby blue. Piperidine (5 ml, 50 mmol) was then added dropwise over 3 minutes. The volume of solution was reduced to 100 ml after being stirred and warmed in room temperature for 3 hrs. The white precipitate was separated and washed with 2 M HCl (3×25 ml) and with water (1×30 ml) to obtain the free acid. Flash chromatography of the crude acid over silica gel (5×40 cm), using hexane-EtOAC (3:1), afforded 1 (5.5 g, 41%) as a colorless crystal m.p. 115–117° C.; FTIR (neat film) $\upsilon_{max}$ [cm$^{-1}$] 3400, 2960, 2868, 1736, 1716, 1249; $^1$H NMR (CDCl$_3$, 300 MHz) δ[ppm]: 9.89(broad), 5.29 (brs, 1H), 3.11 (dd, 1H, J=14.4, 4.3 Hz), 2.33 (d, 1H, J=14.5 Hz), 2.08 (s, 3H), 0.99 (s, 3H), 0.88 (d, 3H, J=6.4 Hz), 0.83 (d, 6H, J=6.6 Hz), 0.65 (s, 3H); $^{13}$C NMR and DEPT (CDCl$_3$, 100 Hz) δ216.4(C), 178.6(C), 170.3(C), 73.5(CH), 55.9(CH), 54.4(CH), 52.3(C), 43.1 (CH$_2$), 42.5(C), 41.5(CH), 39.7(CH$_2$), 39.4(CH$_2$), 35.9 (CH$_2$), 35.7(CH), 35.5(CH), 34.4(CH$_2$), 34.1(CH$_2$), 27.9 (CH), 27.9(CH$_2$), 25.1(CH$_2$), 24.3 (CH$_2$), 23.7(CH$_2$), 23.0 (CH$_2$), 22.8(CH$_3$), 22.5(CH$_3$), 21.5 (CH$_3$), 18.5(CH$_3$), 17.6 (CH$_3$), 11.6(CH$_3$); EIMS (I=1.7v), m/z (relative intensity) 416.4 (M$^+$, 43), 398.4 (M$^+$-H$_2$O, 21), 306.3 (34), 247.3 (97), 110.1 (100); CIMS m/z (I=2.1 v), m/z (relative intensity) 417.4 (M$^+$+1, 88), 399.3 (100), 357.3 (40), 331.3 (45).

Synthesis of 3-β-Acetoxy-B-homo-6-oxa-4-cholesten-7-one (2)

SOCl$_2$ (0.8 ml, 10 mmol) in 2 ml CH$_2$Cl was added dropwise to a stirred and cooled (0° C.) solution of 1 (2.3 g, 5 mmol) in 12 ml CH$_2$Cl$_2$. After the mixture was stirred at 0° C. for 30 min. 0.1 ml of pyridine was added and the resulting mixture was stirred at room temperature for 2 hrs. Then the solvent was evaporated in vacuo to yield a residue which was chromatographed on silica gel to yield 2 (1.92 g, 78%) as colorless oil: [α]$^{20}_D$ +17.7° (c 0.3, CHCl$_3$); uv $\upsilon_{max}$ (CHCl$_3$) 241.6 nm (ε=358); FTIR (neat film) $\upsilon_{max}$ [cm$^{-1}$]: 2939, 2873, 1766, 1740, 1667, 1648, 1375, 1242, 1123; $^1$H NMR (CDCl$_3$, 300 MHz) δ [ppm]: 5.50 (d, 1H, J=4.2 Hz), 5.33(t, 1H, J=3.3 Hz), 2.37 (m, 2H), 2.04 (s, 3H), 1.03 (s, 3H), 0.88 (d, 3H, J=6.6 Hz), 0.85 (d, 6H, J=6.6 Hz) 0.68 (s, 3H); EI HRMS m/z calcd for C$_{29}$H$_{46}$O$_4$ 458.3396, found 458.3408; EIMS (I=1.7v), m/z (relative intensity) 458.3 (22), 498.4 (35), 370.4 (100), 110.1 (62).

Synthesis of 3-α-Azido-B-homo-6-oxa-4,5-cholesten-7-one (3)

To a stirred solution of 2.40 g (5 mmol) crude 2 in 35 ml acetone was added dropwise a solution of NaN$_3$ (650 mg, 10 mmol) in 5 ml water. The reaction mixture was stirred at room temperature for two hours, poured into 50 ml water, and extracted with ether. The ethereal extracts were dried over MgSO$_4$ and concentrated in vacuo to yield a residue which was subjected to silica gel column chromatography (230–400 mesh, hexane/EtOAC=10:1) to afford 3 1.17 g (55.3%) as a yellowish oil: [α]$^{20}$D +98.3° (c 0.6, CHCl$_3$); uv $\lambda_{max}$ (CHCl$_3$) 245 nm (ε=899) ; FTIR (neat film) $\upsilon_{max}$ [cm$^{-1}$]: 2949, 2873, 2094, 1763, 1670, 1247; $^1$H NMR (CDCl$_3$, 300 MHz) δ [ppm]: 5.43 (d, 1H, J=2.5 Hz), 4.07 (m, 1H), 2.44 (d, 1H, J=15.0, 11.0 Hz), 2.38 (dd, 1H, J=15.0, 2.0 Hz), 0.99 (s, 3H), 0.89 (d, 3H, J=6.5 Hz), 0.84 (d, 6H, J=6.6 Hz), 0.65 (s, 3H); $^{13}$C NMR and DEPT (CDCl$_3$, 100 Hz) δ172.1(C), 160.0(C), 113.5(CH), 57.4(CH), 56.3(CH), 55.4 (CH), 51.7(CH), 42.9(C), 39.5(CH$_2$), 39.4(CH$_2$), 39.0(C), 37.0(CH$_2$), 35.9(CH$_2$), 35.6(CH), 34.9(CH), 33.9(CH$_2$), 28.0(CH$_2$), 27.6(CH$_2$), 25.0(CH$_2$), 23.8(CH$_2$), 23.7(CH$_2$), 22.8(CH$_3$), 22.6(CH$_3$), 22.5(CH$_2$), 19.2(CH$_3$), 18.5(CH$_3$), 11.8(CH$_3$); EIMS (1=4.0v), m/z (relative intensity) 413.3 (M$^+$—N$_2$, 46), 399.3 (M$^+$—N$_3$, 100), 385.3 (38), 353.3 (33), 247.2 (22); CIMS m/z (I=1.8v), m/z (relative intensity) 442.2 (M$^+$+1, 17), 414.2 (M$^+$—N$_2$+1, 100), 399.2 (M$^+$—N$_3$, 26); EI HRMS m/z calc. for C$_{27}$H$_{44}$N$_3$O$_2$ 442.3434, found 442.3512.

EXAMPLE 2

Syntheses and Purification of Seco-Cholestane Derivatives (Compounds 4–12)

A solution of 3 (440 mg, 1 mmol) in 1.5 ml EtOAC was poured onto 1.5 g silica gel (0.040–0.063 mm, EM Science Co.). The silica gel was allowed to evaporate the solvent in the hood. Then the 3-α-azido-B-homo-6-oxa-4,5-cholesten-7-one (3) coated silica gel was heated in a preheated oven at 180° C. for 1 hour, then extracted with EtOAc (50 mL) and methanol (2×5 mL). The resulting solutions were combined and concentrated in vacuo to yield a residue which was subject to column chromatography (silica gel 230–400 mesh, hexane/EtOAC=20:1–3:1) to afford 4 (25 mg, 6.28%) and 249 mg of crude mixture of compounds 5–12, which were further purified carefully by flash chromatography on silica gel (10 microns), and preparative thin layer chromatography (silica gel, Whatman Co., Hexane/EtOAc=2:1) for several times to afford 5 (56 mg, 13.5%), 6 (44 mg, 10.7%), 7 (10.0 mg, 3.61%), 8 (51 mg, 12.3%), 9 (40 mg, 9.3%), 10 (38 mg, 9.2%). Compounds 11 and 12 are very likely to form in the pyrolysis process. However, the yield was low because there is only one proton at C9 of the pyrolysis precursor. 6-Oxa-2, 3–4, 5-cholest-dien-7-one (4) was obtained as colorless oil: FTIR (neat film) $\upsilon_{max}$ [cm$^{-1}$]: 2947, 2847, 1768, 1657; $^1$H NMR (CDCl$_3$, 300 MHz) δ [ppm]: 5.91 (ddd, 1H, J=5.7, 3.6, 3.5 Hz), 5.69 (d, 1H, J=5.5 Hz), 5.67 (ddd, 1H, J=5.7, 5.4, 2.5 Hz), 2.50 (d, 1H, J=12.3 Hz), 2.37 (d, 1H, J=12.4 Hz), 2.47 (d, 1H, J=18.3 Hz), 2.27 (d, J=17.5, 2.8 Hz), 1.02 (s, 3H), 0.89 (d, 3H, J=6.5 Hz), 0.86 (d, 6H, J=6.5 Hz), 0.68 (s, 3H); $^{13}$C NMR and DEPT (CDCl$_3$, 100 Hz) δ173.4(C), 157.6(C), 123.5(CH), 123.2 (CH), 111.6(CH), 56.4(CH), 55.4(CH), 45.9(CH), 43.1(C), 39.4(CH$_2$), 39.4(CH$_2$), 37.8(C), 37.2(CH$_2$), 36.3(CH$_2$), 35.6 (CH), 35.1(CH), 28.0(CH), 27.7(CH$_2$), 25.0(CH$_2$), 23.8 (CH$_2$), 22.8(CH$_2$), 22.8 (CH$_3$), 22.5(CH$_3$), 18.6(CH$_3$), 18.0 (CH$_3$), 17.9 (CH$_2$), 11.9(CH$_3$); EIMS (I=1.3v), m/z (relative intensity) 398.4 (M$^+$, 20), 370.4 (10), 329.4 (22), 247.3 (23), 149.2 (40), 109.1 (100); HRMS m/z calcd for C$_{27}$H$_{42}$O$_2$ 398.3185, found 398.3187.

5,6-Seco-5-oxo-3,4-cholesten-6-oic acid (5) was obtained as colorless oil: FTIR (neat film) 2916, 1747, 1712, 1677, 1466, 1389, 1228; $^1$H NMR (CDCl$_3$, 300 MHz) δ [ppm]: 6.73 (m, 1H), 5.88 (dd, 1H, J=10.5, 1.5 Hz), 2.40 (dd, 1H, J=15.5, 5.0 Hz), 1.10 (s, 3H), 0.90 (d, 3H, J=6.5 Hz), 0.86 (d, 6H, J=6.6 Hz), 0.69 (s, 3H); EIMS (I=7.0 v), m/z (relative intensity) 416.3 (M$^+$, 17), 398.3 (23), 354.3 (32), 333.3 (55), 247.3 (63), 110.1 (100); CIMS m/z (I=223 mv), m/z (relative intensity) 417.3 (7), 399.3 (80), 153.1 (83), 110.1 (100); HRMS m/z calcd for C$_{27}$H$_{44}$O$_3$ 416.3290, found 416.3272. The synthesis of this compound through other methods were published: Medelovici, M., Glotter, E., *J. Chem. Soc. Perkin Trans.* 1, 13, 1992; 1735–1740; Nace, H. R., Capstack, E., JOCEAH, *J. Org. Chem.*, 1961, 26, 5020–5024.

Compound 6 was obtained as colorless prisms: mp.= 109–111° C.; [α]$^{20}$D −42.1° (c 0.73, CHCl$_3$); uv λmax (CHCl$_3$) 240.8 nm (ε=89.7); FTIR (neat film) $\upsilon_{max}$ [cm$^{-1}$]: 3071, 2956, 2871, 2219, 1720, 1390, 1259; $^1$H NMR (CDCl$_3$, 300 MHz) δ [ppm]: 6.52 (dt, 1H, J=10.8, 7.8 Hz), 5.32 (d, 1H, J=10.5 Hz), 2.60 (dd, 1H, J=17.7, 4.8 Hz), 2.55 (m, 2H), 2.07 (dt, 2H, J=12.0, 2.7 Hz), 2.00 (dd, 1H, J=17.7 11.5 Hz), 1.99–1.77 (m, 5H), 1.34 (s, 3H), 0.90 (d, 3H, J=6.0 Hz), 0.86 (d, 6H, J=6.6 Hz), 0.70 (s, 3H); $^{13}$C NMR and DEPT (CDCl$_3$, 100 Hz) δ170.8(C), 154.5(C), 115.9(C), 99.8(CH), 86.6(C), 55.7(CH), 55.6(CH), 44.5(CH), 42.5(C), 39.4($CH_2$), 38.9($CH_2$), 38.2($CH_2$), 36.0($CH_2$), 35.7($CH_2$), 35.6(CH), 30.8(CH), 28.0($CH_2$), 28.0(CH), 25.8($CH_2$), 23.7 ($CH_2$), 23.5($CH_2$), 23.0($CH_3$), 22.8($CH_3$), 22.8($CH_2$), 22.5 ($CH_3$), 18.6($CH_3$), 11.9($CH_3$); EIMS (I=5.4 v), m/z (relative intensity) 413.3 ($M^+$, 5), 398.3 (2), 385.3 (2), 353.3 (5), 333.3 (46), 290.2 (21), 248.2 (28), 135.1 (100); CIMS m/z (I=3.5 v), m/z (relative intensity) 414.3 ($M^+$+1, 100), 396.3 (37), 333.3 (18), 135.1 (22); EI HRMS m/z calcd. for $C_{27}H_{43}NO_2$ 413.3294, found 413.3253; Anal. Calcd for $C_{27}H_{43}NO_2$: C, 78.39; H, 10.48; N, 3.39; found: C, 78.66; H, 10.71; N, 3.42.

Compound 7 was obtained as colorless prisms: m.p. =132–134° C.; $[\alpha]^{20}_D$ +39.3° (c 0.52, $CHCl_3$); uv λmax ($CHCl_3$) 242.6 nm ($\epsilon$=152); FTIR (neat film) $\upsilon_{max}$ [$cm^{-1}$]: 2954, 2870, 2224, 1733, 1473, 1389, 1256; $^1$H NMR ($CDCl_3$, 300 MHz) δ [ppm]: 6.54 (dt, 1H, J=11.0, 7.8 Hz), 5.35 (d, 1H, J=11.1 Hz), 2.63 (dd, 2H, J=15.4, 9.0 Hz), 2.61 (dd, 1H, J=18.0, 5.1 Hz), 2.02 (dd, 1H, J=18.0, 11.5 Hz), 2.01–1.68 (m, 5H), 1.43 (s, 3H), 0.91 (d, 3H, J=6.6 Hz), 0.86 (d, 6H, J=6.3 Hz), 0.70 (s, 3H); $^{13}$C NMR and DEPT ($CDCl_3$, 100 Hz) δ 170.6(C), 154.4(CH), 115.8(C), 100.2 (CH), 86.3(C), 55.9(CH), 55.8(CH), 49.3(CH), 42.6(C), 39.4($CH_2$), 39.1($CH_2$), 36.0($CH_2$), 35.7($CH_2$), 35.6(CH), 34.8($CH_2$), 30.9(CH), 28.1($CH_2$), 28.0(CH), 26.1($CH_2$), 26.0($CH_3$), 23.8($CH_2$), 23.4($CH_2$), 22.9($CH_2$), 22.8($CH_3$), 22.5($CH_3$), 18.7($CH_3$), 12.0($CH_3$); EIMS (I=1.4 v), m/z (relative intensity) 413.5 ($M^+$, 45), 398.5 (24), 385.5 (27), 333.4 (31), 248.3 (33), 135.2 (100); EI HRMS m/z calcd. for $C_{27}H_{43}NO_2$ 413.3294, found 413.3308; Anal. Calcd. for $C_{27}H_{43}NO_2$: C, 78.39; H, 10.48; N, 3.39; found: C, 78.31; H, 10.41. N, 3.34.

Compound 8 was obtained as colorless oil: $[\alpha]^{20}$D +31.0° (c 0.35, $CHCl_3$); uv λmax ($CHCl_3$) 240.8 nm ($\epsilon$=814); FTIR (neat film) $\upsilon_{max}$ [$cm^{-1}$]: 3380, 3728, 2953, 2874, 2229, 1703, 1459, 1288; $^1$H NMR ($CDCl_3$, 300 MHz) δ [ppm]: 6.50 (dt, 1H, J=11.0, 7.2 Hz), 5.33 (d, 1H, J=11.0 Hz), 4.93(s, 1H), 4.84(s, 1H), 2.59 (m, 2H), 2.35 (dd, 1H, J=15.0, 3.3 Hz), 2.10 (dd, 1H, J=15.0, 11.5 Hz), 2.17 (t, 2H, J=7.2 Hz), 1.97 (m, 3H), 0.90 (d, 3H, J=6.6 Hz), 0.86 (d, 6H, J=6.6 Hz), 0.68 (s, 3H); $^{13}$C NMR and DEPT ($CDCl_3$, 100 Hz) δ 179.1(C), 154.7(CH), 150.2(C), 116.0(C), 111.2($CH_2$), 99.8 (CH), 56.0(CH), 55.3(CH), 51.4(CH), 43.0(C), 39.6($CH_2$), 39.5($CH_2$), 37.2 ($CH_2$), 36.1($CH_2$), 35.8(CH), 35.7(CH), 32.5 ($CH_2$), 29.9($CH_2$), 29.0($CH_2$), 28.0(CH), 28.0($CH_2$), 24.4($CH_2$), 23.8($CH_2$), 22.8($CH_3$), 22.5($CH_3$), 18.7 ($CH_3$), 11.9($CH_3$); EIMS (I=4.2 v), m/z (relative intensity) 413.3 ($M^+$, 34), 395.3 (100), 380.3 (25), 354.3 (67), 333.3 (23), 282.2 (44), 240.2 (40), 43.0 (98); CIMS m/z (I=1.7 v), m/z (relative intensity) 414.4 ($M^+$+1, 100), 396.4 (78), 378.4 (18), 349.4 (21); EI HRMS m/z calcd. for $C_{27}H_{43}NO_2$ 413.3294, found 413.3279; Anal. Calcd for $C_{27}H_{43}NO_2$: C, 78.39; H, 10.48; N, 3.39; found: C, 78.26; H, 10.39; N, 3.36.

The relative stereostructure of compound 7 was determined by single-crystal X-ray diffraction. Compound 7 was crystallized in space group $P2_12_12_1$ with a=6.467(2) Å, b=34.103(1) Å, c=35.479(1) Å and refined to a conventional factor R=0.0069 for 867 parameters and 10471 reflections with $F_o$>4 sigma ($F_o$).

Compound 9 was obtained as colorless oil. $[\alpha]^{20}_D$ +12.7° (c 0.15, $CHCl_3$); uv λmax ($CHCl_3$) 255.0 nm ($\epsilon$=1067) ; FTIR (neat film) $\upsilon_{max}$ [$cm^{-1}$]: 2955, 2874, 2224, 1711, 1649, 1470, 1386, 1292; $^1$H NMR ($CDCl_3$, 300 MHz) δ [ppm]: 6.37(dt, 1H, J=10.9, 7.7 Hz), 5.27 (dd, H, J=9.4 Hz, 1.1 Hz), 5.18 (t, J=7.7 Hz) 3.10 (dt, 2H, J=7.7 Hz, 5.5 Hz), 1.67 (s, 3H), 0.90 (d, 3H, J=6.6 Hz), 0.86 (d, 6H, J=6.6 Hz), 0.68 (s, 3H); EIMS (I=1.1 v), m/z (relative intensity): 413(15), 395(28), 354(25), 333(12), 240(17), 43(100); EI HRMS m/z calcd for $C_{27}H_{43}NO_2$ 413.3294, found 413.3312. Anal. Calcd. for $C_{27}H_{43}NO_2$:C, 78.39; H, 10.48; N, 3.39; found: C, 78.35; H, 10.41; N, 3.40. The configuration of the 1,10 double bond was assigned as Z for the NOE observed between Me-19 and H-1 in the NOESY spectrum.

Compound 10 was obtained as colorless oil. $[\alpha]^{20}_D$ +26.6° (c 0.30, $CHCl_3$); uv λmax ($CHCl_3$) 255.4 nm ($\epsilon$=1212); FTIR (neat film) $\upsilon_{max}$ [$cm^{-1}$]: 2946, 2871, 2221, 1704, 1704, 1647, 1470, 1388, 1294; $^1$H NMR ($CDCl_3$, 300 MHz) δ [ppm]: 6.38 (dt, 1H, J=11.1, 7.5 Hz), 5.27 (d, H, J=10.4 Hz), 5.17 (t, J=7.2 Hz), 3.08 (t, 2H, J=7.2 Hz), 1.60 (s, 3H), 0.90 (d, 3H, J=6.6 Hz), 0.86 (d, 6H, J=6.6 Hz), 0.68 (s, 3H); EIMS (I=1.5 v), m/z (relative intensity): 413(20), 395(57), 354(50), 333(12), 282(32), 240(32), 43(100); EI HRMS m/z calcd for $C_{27}H_{43}NO_2$ 413.3294, found 413.3271; Anal. Calcd. for $C_{27}H_{43}NO_2$:C, 78.39; H, 10.48; N, 3.39; found: C, 78.29; H, 10.45; N, 3.42.

EXAMPLE 3

Hydrogenation to Produce Additional Cholestane

Derivatives (Compounds 13, 14, and 15)

To a solution of Compound 8 (25 mg, 0.061 mmol) in 5 ml ethyl acetate was added 5 mg of 10% Pd/C. The resulting mixture was stirred and hydrogenated for 30 minutes to absorb one equivalent of hydrogen, filtered through Celite. The filtrate was concentrated in vacuo to yield 23 mg of Compound 13 (92%) as colorless oil. $[\alpha]^{20}_D$ +38.9° (c 0.15, $CHCl_3$); $^1$H NMR ($CDCl_3$, 300 MHz) δ [ppm]: 4.84(d, 2H, J=22.4 Hz), 2.35(m, 4H), 0.95 (d, 3H, J=6.6 Hz), 0.85 (d, 6H, J=6.6 Hz), 0.75(s, 3H); $^{13}$C NMR ($CDCl_3$, 100 MHz) δ 179.1, 151.3, 119.7, 110.5, 56.0, 55.4, 51.4, 43.1, 39.7, 39.5, 37.3, 36.1, 35.9, 35.7, 29.3, 28.0, 28.0, 27.9, 26.9, 25.2, 24.4, 23.8, 22.8, 22.5, 18.7, 17.1, 12.0; EIMS (I=1.4 v), m/z (relative intensity): 415(15), 397(53), 369(28), 355(50), 305(100), 242(80),135(93); EI HRMS m/z calcd for $C_{27}H_{45}NO_2$ 415.3450, found 415.3451.

To a solution of Compound 6 (40 mg, 0.097 mmol) in 8 ml ethyl acetate was added 10 mg of 10% Pd/C. The resulting mixture was stirred and hydrogenated for 40 minutes filtered through Celite. The filtrate was concentrated in vacuo to yield 38 mg of Compound 15 (92%) as colorless oil. $[\alpha]^{20}_D$ −9.2° (c 0.5, $CHCl_3$); $\upsilon_{max}$ [$cm^{-1}$]: 2952, 2873, 2250, 1726, 1468, 1388, 1256, 977; $^1$H NMR ($CDCl_3$, 300 MHz) δ [ppm]: 2.60(dd, 1H, J=17.7,4.8 Hz), 2.36(t, 2H, J=6.6 Hz), 2.06(m, 1H), 1.97(dd, 1H, J=17.7, 11.4), 1.31 (s, 3H), 0.90(d, 3H, J=6.6 Hz), 0.86(d, 6H, J=6.6 Hz) 0.70(s, 3H); EIMS (I=5.9 v), m/z (relative intensity): 415(12), 400(22), 355(15), 333(38), 248(30), 135(100); CI HRMS m/z calcd for $C_{27}H_{46}NO_2$ 416.3529, found 416.3520.

To a solution of Compound 8 (25 mg, 0.061 mmol) in 5 ml ethyl acetate was added 5 mg of 10% Pd/C. The resulting mixture was stirred and hydrogenated for 72 hours, filtered through Celite. The filtrate was concentrated in vacuo and separated by reverse phase HPLC using 100% aceonitrile to afford 10 mg of compound 14S as colorless oil: $^1$H NMR ($CDCl_3$, 300 MHz) δ[ppm]: 2.31(m, 2H), 1.94(m, 1H), 0.88(d, J=6.6 Hz, 3H), 0.84(d, J=6.6 Hz, 3H), 0.78(d, J=7.2 Hz, 3H), 0.66(s, 3H); $^{13}$C NMR ($CDCl_3$, 100 MHz) δ 179.1, 119.8, 56.1, 54.8, 44.8, 43.0, 39.5, 39.4, 36.1, 35.7, 35.5, 34.9, 31.9, 28.0, 27.9, 26.8, 25.5, 24.8, 23.8, 22.8, 22.5, 20.2, 18.7, 17.1, 13.6, 11.7; FABMS (I=1.5 V), m/z (relative intensity) : 418 ($M^+$+1, 25), 400 (100), 382(45), 356(20); FAB HRMS calcd for $C_{27}H_{48}NO_2$, 418.3771, found 418.3679; and 8 mg of compound 14R as colorless oil: $^1$H NMR ($CDCl_3$, 300 MHz) δ[ppm]: 2.32(t, J=6.9 Hz, 2H), 2.24(d, J=4.8 Hz, 2H), 1.94(m, 1H), 0.89(d, J=6.6 Hz, 3H), 0.88 (d, J=6.6 Hz, 3H), 0.84(d, J=6.6 Hz, 3H), 0.67(s, 3H); $^{13}$C NMR (CDCl$_3$, 100 MHz) δ178.9, 120.1, 56.2, 55.3, 48.9, 43.0, 39.6, 39.5, 37.1, 36.1, 35.8, 35.5, 29.5, 28.0, 27.9, 27.4, 25.7, 24.8, 23.8, 22.8, 22.5, 21.0, 19.0, 18.7, 17.1, 11.9; FABMS (I=1.3 V), m/z (relative intensity): 418 (M$^+$+1, 32), 400 (100), 382(55), 356(35) FAB HRMS calcd for C$_{27}$H$_{48}$NO$_2$, 418.3771, found 418.3683.

To a solution of a mixture of 9 and 10 (1:1), (40 mg, 0.097 mmol) in 8 ml ethyl acetate was added 10 mg of 10% Pd/C. The resulting mixture was stirred and hydrogenated for about 40 min, the reaction was stopped after the reactants absorbed one equiv. of hydrogen. The products were filtered through Celite and concentrated in vacuo and separated by reverse phase HPLC using 100% acetonitrile to afford 20 mg of compound 17 as colorless oil: $^1$H NMR (CDCl$_3$, 300 MHz) δ[ppm]: 5.11(t, J=6.9 Hz, 1H), 2.30(t, J=7.2 Hz, 2H), 2.21~1.93(m, 6H), 1.65(s, 3H), 0.88(d, J=6.6 Hz, 3H), 0.84(d, J=6.6 Hz, 3H), 0.72(s, 3H); $^{13}$C NMR (CDCl$_3$, 100 MHz) δ 178.2, 139.8, 125.1, 119.7, 56.0, 55.2, 44.4, 43.1, 39.5, 39.5, 37.0, 36.1, 35.7, 34.9, 28.0, 27.9, 26.8, 26.2, 25.6, 24.4, 23.8, 22.8, 22.5, 19.2, 18.7, 16.6, 11.9; and 19.5 mg of compound 18 as colorless oil: $^1$H NMR (CDCl$_3$, 300 MHz) δ[ppm]: 5.13(t, J=6.9 Hz, 1H), 2.30(t, J=7.2 Hz, 2H), 2.26~2.02(m, 4H), 1.94(m, 2H), 1.55(s, 3H), 0.88(d, J=6.6 Hz, 3H), 0.84(d, J=6.6 Hz, 3H), 0.72(s, 3H); $^{13}$C NMR (CDCl$_3$, 100 MHz) δ 178.5, 140.0, 124.2, 119.9, 56.1, 55.0, 54.0, 43.1, 39.5, 39.5, 37.3, 36.0, 35.7, 35.2, 28.0, 28.8, 27.8, 26.5, 25.3, 24.6, 23.8, 22.8, 22.5, 18.7, 16.5, 12.9, 11.9.

EXAMPLE 4

Base Catalysed Hydrolysis and Michael Addition Reactions to Produce

Additional Seco-cholestane Derivatives

A solution of 25 mg (0.06 mmol)compound 6 in 10 ml of 0.6% sodium hydroxide in methanol was heated under reflux for overnight. The solution was carefully acidified with 2 M HCl, then 6 ml of ethyl ether was added to precipitate the NaCl formed. The solution was filtered, dried over anhydrous sodium sulfate, and evaporated at reduced pressure. The residue was subjected to silica gel (200–240 mesh) column chromatogrphy, eluted with Hexane: EtOAc=3:1 to afford compound 22 (3S, 5 mg, 19%) as colorless crystal: m.p.=144~145° C.; FTIR (neat film) υ$_{max}$ [cm$^{-1}$]: 2956, 2937, 2859, 2250, 1700, 1464, 1383, 1290, 1066; $^1$H NMR (CDCl3, 300 MHz) δ [ppm]: 4.21 (m, 1H), 2.65 (m, 3H), 2.44(dd, J=14.6, 4.4 Hz, 1H); 1.25(s, 3H), 0.87(d, J=6.6 Hz), 0.85(d, J=6.6 Hz, 6H), 0.68(s, 3H); FAB MS (I=0.93 v) m/z (relative intensity): 432(40, M$^+$+1), 414(100), 396(20), 373 (20);

Compound 21 (3R, 3 mg, 12%) as colorless oil: $^1$H NMR (CDCl3, 300 MHz) δ [ppm]: 4.37 (m, 1H), 2.64 (m, 3H), 2.44(dd, J =14.6, 4.4 Hz, 1H); 1.25(s, 3H), 0.87(d, J=6.6 Hz), 0.85(d, J=6.6 Hz, 6H), 0.68(s, 3H); CIMS (I=5.2 v) m/z (relative intensity): 432 (20, M$^+$+1), 414(100), 396(10), 157(10), 124(74);

Mixture of Compounds 23 and 24 10 mg(37%, 3R: 3S=1:1) as colorless oil: FTIR (neat film) υ$_{max}$[cm$^{-1}$]: 2951, 2869, 1725, 1700, 1466, 1380, 1281, 1111; $^1$H NMR (CDCl3, 300 MHz) δ [ppm]: 3.44(m, 1H), 3.42(m, 1H), 3.38(s, 3H), 3.37(s, 3H), 2.59(dd, J=18.0, 4.8, 2H), 2.50, m, 4H), 1.95(dd, J=17.4, 12.0, 2H), 1.32(s, 3H), 1.30(s, 3H), 0.95(d, J=6.6 Hz, 6H), 0.87(d, J=6.6 Hz, 12H), 0.68(s, 6H); FABMS (I=0.6 v) m/z (relative intensity): 446 (M$^+$+1, 100), 429(45), 413(8), 396(5), 323(47).

A solution of 25 mg (0.06 mmol) compound 15 in 10 ml of 6% sodium hydroxide in aqueous methanol was heated under reflux for overnight. The solution was carefully acidified with 2 M HCl until there are white precipitates formed. The solution was extracted with ethyl ether, dried over anhydrous sodium sulfate, and evaporated under pressure. The residue was purified using preparative TLC to afford compound 27 17 mg (65%) as colorless oil: FTIR (neat film) υ$_{max}$[cm$^{-1}$]: 2950, 2870, 1733, 1716, 1459, 1382, 1259; $^1$H NMR (CDCl3, 300 MHz) δ [ppm]: 2.58(dd, J=17.7, 5.1 Hz, 1H), 2.35(t, J=7.2 Hz, 2H), 2.04(d, J=12 Hz, 2H), 1.95(dd, J=17.7, 12.0 Hz, 1H), 1.30(s, 3H), 0.90(d, J=6.6 Hz, 3H), 0.85(d, J=6.6 Hz, 6H), 0.69(s, 3H) FAB MS (I=0.93v) m/z (relative intensity): 435 (M$^+$+1, 100), 417(18), 399(15), 375(12), 323(10).

EXAMPLE 5

Inhibition of CDC25A Phosphatase

The production and purification of GST fusion protein and CDC25A phosphatase inhibition assays were performed as previously described. Rice, R. L. et al., *A targeted Library of Small-Molecule, Tyrosine, and Dual-Specificity Phosphatase Inhibitors Derived from a Rational Core Design and Random Side Chain Variation*, Biochemistry, 1997, 36, 15965–15974. Briefly, the target enzyme for the assay was a glutathione S-transferase (GST) fusion protein containing the full length sequence for human cdc25A. The enzyme was expressed in *Escherichia coli* and purified by affinity chromatography over glutathione-agarose. Enzyme activity was measured under linear reaction conditions with fluorescein diphosphate as the substrate. Reactions were performed in the presence of 10 mM dithiothreitol to eliminate oxidant-type inhibitors from scoring as hits in this assay. A structurally related compound, 3-actoxy-5, 6-seco-5-oxo-pregnen-6-oic acid, show no inhibitory activity against CDC25A phosphatase, and was used as negative control in the assay. The concentrations of each compound yielding 50% inhibition of cdc25A was as follows:

| Compound ID | Approximate IC$_{50}$ (µg per ml) |
| --- | --- |
| 8 | 4.4 |
| 9 | >10 |
| 10 | 10 |
| 6 | 6 |
| 7 | >50 |
| 13 | 0.9 |
| 15 | 0.9 |

The IC$_{50}$s of these compounds showed that the cholesteyl side chain is essential for the activity of these compounds. The negative control compound, 3-actoxy-5, 6-seco-5-oxo-pregnen-6-oic acid, lost its activity due to the removal of the cholesteryl side chain. In addition, the configuration of the cyano-containing side chain is very important for the inhibitory activity of these compound: with the more flexible cyano side chain conformation, Compounds 13 and 15 are much more potent than the double bond unsaturated compound in this series. Furthermore, the configuration of C10 needs to be an R, because compound 7 (10S) was much less active than the 10R isomer, compound 6.

EXAMPLE 6

Inhibition of the Growth of Human Colon Cancer Cells

Compounds 6 and 8 prepared as discussed in the preceding examples were also evaluated for potency as inhibitors of colon cancer cell lines (HT-29). Inhibition of HT-29 colon carcinoma cell growth by compounds 6 and 8 was measured in the soft agarose colony-forming assay with continuous drug exposure over 7 days as previously described. Alley M. C. et al., *Activation and inactivation of cancer chemotherapeutic agents by rat heptocytes cocultured with human tumor cell lines,* Cancer Res 44:549 (1984). Briefly, soft-agarose culture was performed in 35-mm culture dishes contained a base layer consisting of 0.5 ml of standard culture medium with 0.5% agarose. On day 0, cells in log-phase growth were dissociated with trypsin and EDTA, washed once in growth medium, and subcultured by layering $1 \times 10^4$ viable cells in 0.5 ml of growth medium, with 0.3% agarose over each base layer. Cultures containing uniformly distributed single-cell suspensions were accepted for subsequent evaluation. On day one compounds were applied to each culture. Cell lines forming a sufficient number of detectable colonies were analyzed following 7 days of incubation. Viable colonies were stained using metabolizable tetrazolium salt, and analyzed as described previously. Alley, M. C. et al., *Improved detection of drug cytotoxicity in the soft agar colony formation assay through use of a metabolizable tetrazolium salt,* Life Sci., 3, 3071–3078, 1982. FIG. 5 shows that compounds 8 and 6 inhibit the proliferation of HT-29 colon cancer cells with $IC_{50}$ values of 4.8 μg/ml and 5 μg/ml, respectively.

EXAMPLE 7

Inhibition of Growth of Lung Adenocarcinoma (A-549) Cells

Figure 6:
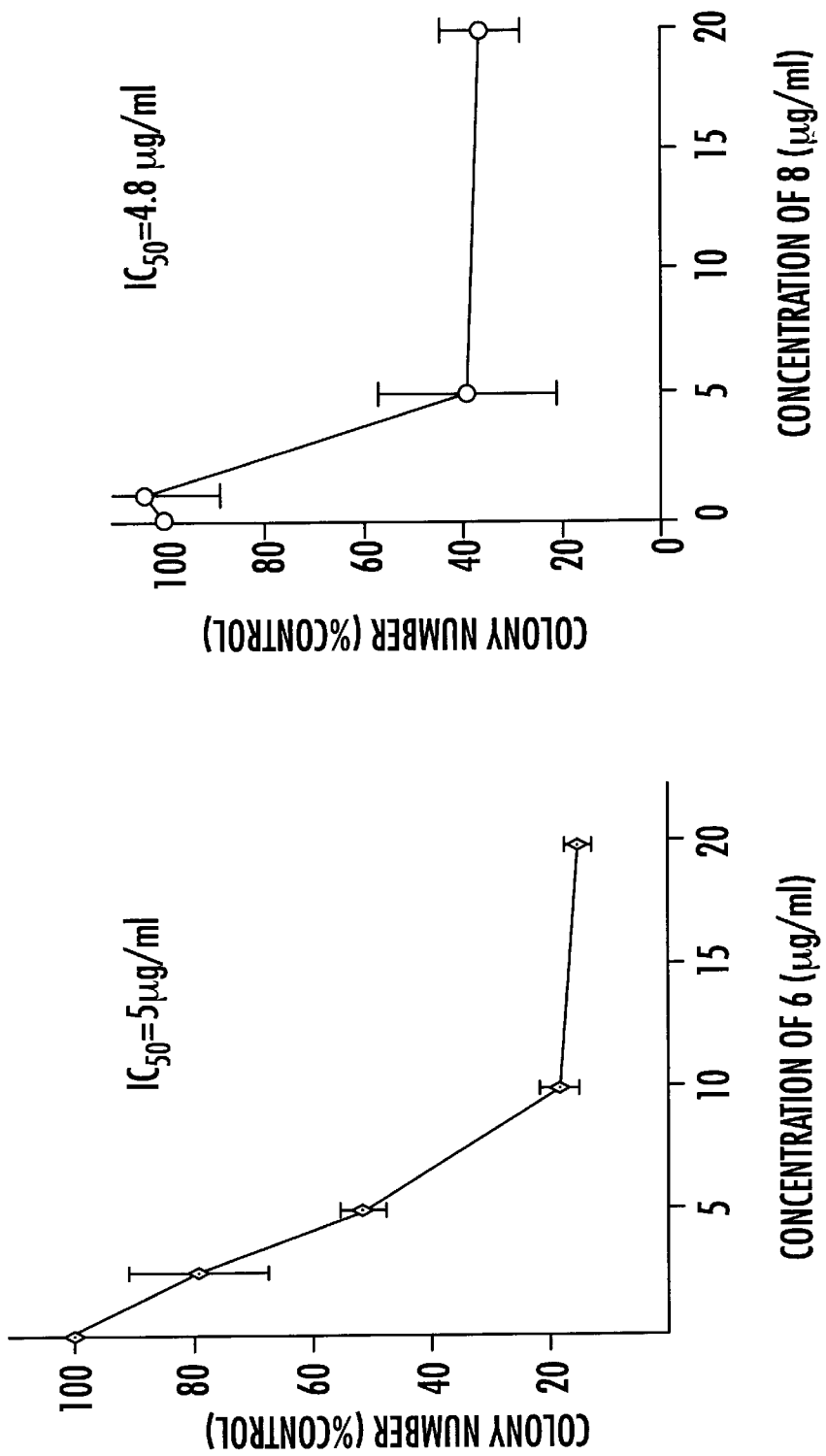
FIG. 6 is a graph illustrating the inhibition of HT-29 colon cancer cells by seco-cholestane derivatives of the invention.
Figure 7:
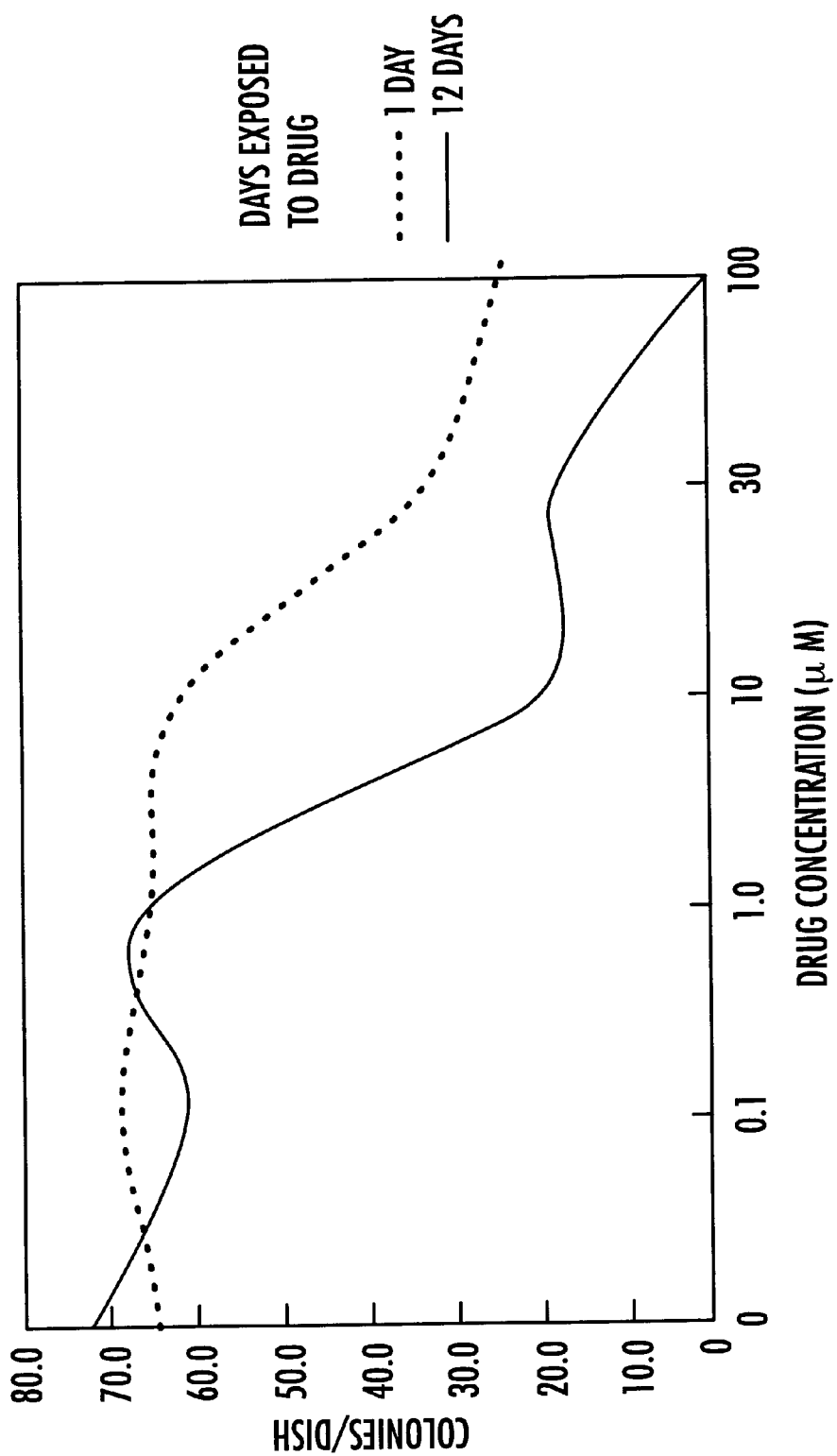
FIG. 7 is a graph illustrating the inhibition of A459 lung adenocarcinoma cells by a seco-cholestane derivative of the invention.

Compound 6 prepared as discussed in the preceding examples were also evaluated for potency as inhibitors of the growth of lung adenocarcinoma cell lines. The effect of compound 6 was assessed with a clonogenic assay. In brief, A549 cells in log-phase growth were harvested, resuspended in fresh growth media and plated in triplicate in 60 mm dishes at cell concentrations estimated to yield 20–100 colonies per dish following treatment. Four hours after plating, cells were either exposed to compound 6 for one day followed by a wash and culture in fresh medium for 11 days (dotted line), or continuously exposed to this compound for 12 days (solid line). Cells were fixed and stained with Coomassie Blue at the end of the 12th day. Colonies with greater than 50 cells were scored. FIG. 6 shows that in the 12-day exposure to compound 6, the number of A549 colonies per dish were reduced 50% at 7 μM, while one day exposure to this compound followed by a wash and cultured in fresh medium for 11 days, results in 50% reduction of the tumor cell colony number per dish at 37 μM.

The foregoing examples are illustrative of the present invention, and are not to be construed as limiting thereof. The invention is defined by the following claims, with equivalents of the claims to be included therein.

That which is claimed is:

1. A compound of the formula (I)

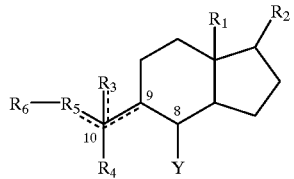

wherein:

$R_1$ is selected from the group consisting of H, lower alkyl, and alkoxy;

$R_2$ is selected from the group consisting of C1–C10 alkyl, substituted C1–C10 alkyl, C2–C10 alkene containing one to four double bonds, substituted C2–C10 alkene, and C1–C10 alkyl or C2–C10 alkene having one or more heteroatoms selected from the group consisting of oxygen atoms and nitrogen atoms inserted into the chain thereof, the chain having 10 or less atoms including the hetero atoms;

$R_3$ is selected from the group consisting of methylene, ketone, and methyl;

$R_4$ is absent when $R_3$ is methylene or ketone, or when $R_3$ is methyl, $R_4$ is selected from the group consisting of hydrogen, lower alkyl, alkoxy, lower alkanoyloxy, hydroxy, carboxyl, amino, lower alkylamino, and halo, or $R_4$ is an oxygen atom which together with the C10 atom to which $R_4$ is attached and $R_5$ consists of a heterocyclic ring and the double bond between C10 and $R_3$, C9 and C10, or C10 and $R_5$ is absent;

Y is selected from the group consisting of C1–C6 alkyl and C2–C6 alkene, said C1–C6 alkyl or C2–C6 alkene terminating in an amide group —$CONH_2$, a nitrile group —CN or an acid group selected from the group consisting of carboxylic acids, sulfonic acids, carbodithioic acids and phosphoric acids, or salts thereof, or Y is —$(CH_2)_n$—C(O)—X—, wherein n is an integer from 1 to 3, X is oxygen or nitrogen, and together with C8 atom to which Y is attached, the C9 atom, and the C10 atom constitute a ring system comprising a 6 to 8 membered lactone or lactam ring, or Y is —$(CH_2)$—C(O)—O—, and together with the C8 atom to which Y is attached, the C9 atom, the C10 atom, and $R_5$ constitute a ring system consisting of a lactone ring when $R_3$ is methyl, $R_4$ is hydroxyl and the double bond between C10 and $R_3$, $R_5$ and C10 or C9 and C10 is absent;

$R_5$ is selected from the group consisting of C2–C8 alkyl, C2–C8 alkene having one or more double bonds, substituted C2–C8 alkyl, and substituted C2–C8 alkene;

$R_6$ is a functional group selected from the group consisting of CN, COOH, CHO, $CH_2OH$, $CONH_2$, CSSH, or salts of these acid groups, and $CONR_2$, wherein R is lower alkyl, acyl or H, and optionally a hydrogen atom of a carbon atom adjacent $R_6$ is replaced with an identical functional group; and the broken lines indicate optional double bonds, and pharmaceutically acceptable salts thereof.

2. The compound of claim 1, wherein said compound has the formula (Ia):

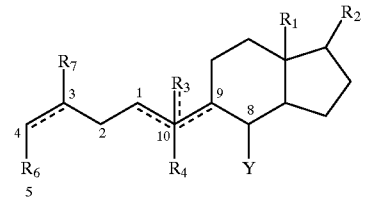

wherein:

$R_1$, $R_2$, $R_3$, $R_4$, $R_6$, and Y are the same as defined above;

$R_5$ is C4 alkyl or C4 alkene having one or more double bonds as indicated by the dotted lines; and $R_7$ is a substituent introduced by Michael Addition of nucleophiles to the double bond between C3 and C4 when present.

3. The compound of claim 2, wherein Y is —$CH_2$—C(O)—OH.

4. The compound of claim 2, wherein Y is —$CH_2$—C(O)—O— and together with the C8 atom to which Y is attached, the C9, and the C10 atoms constitute a ring system comprising a 6 membered lactone ring.

5. The compound of claim 2, wherein Y is —$CH_2$—C(O)—X, wherein X is an oxygen atom, together with the C8 atom to which Y is attached, the C9, C10, C1, C2 atoms, and the C3 atom to which X is attached, constitute a 9 membered lactone ring, when $R_3$ is methyl, $R_4$ is a hydroxyl group, and the double bond between C3 and C4 is absent, and the double bond between C10 and R3, or between C1 and C10, or between C9 and C10 is absent.

6. The compound of claim 3, wherein $R_3$ is =$CH_2$ and the double bond is present between C10 and $R_3$, the double bond is absent between C1 and C10, the double bond is absent between C9 and C10, and the double bond is present between C3 and C4.

7. The compound of claim 3, wherein $R_3$ is —$CH_3$ and the double bond is absent between C10 and $R_3$, the double bond is absent between C9 and C10, the double bond is present between C1 and C10, and the double bond is present between C3 and C4.

8. The compound of claim 7, wherein the double bond between C1 and C10 is in a Z configuration.

9. The compound of claim 7, wherein the double bond between C1 and C10 is in an E configuration.

10. The compound of claim 3, wherein $R_3$ is =$CH_2$ and the double bond is present between C10 and $R_3$, the double bond is absent between C1 and C10, the double bond is absent between C9 and C10, and the double bond is absent between C3 and C4.

11. The compound of claim 3, wherein $R_3$ is —$CH_3$, and the double bond is absent between C10 and $R_3$, the double bond is absent between C9 and C10, the double bond is present between C1 and C10, and the double bond is absent between C3 and C4.

12. The compound of claim 11, wherein the double bond between C1 and C10 is in a Z configuration.

13. The compound of claim 11, wherein the double bond between C1 and C10 is in a E configuration.

14. The compound of claim 3, wherein $R_3$ is —$CH_3$, and the double bond is absent between C10 and $R_3$, the double bond is absent between C1 and C10, the double bond is present between C9 and C10, and the double bond is present between C3 and C4.

15. The compound of claim 14, wherein the double bond between C9 and C10 is in a Z configuration.

16. The compound of claim 14, wherein the double bond between C9 and C10 is in a E configuration.

17. The compound of claim 3, wherein $R_3$ is —$CH_3$, and the double bond is absent between C10 and $R_3$, the double bond is absent between C1 and C10, the double bond is present between C9 and C10, and the double bond is absent between C3 and C4.

18. The compound of claim 17, wherein the double bond between C9 and C10 is in a Z configuration.

19. The compound of claim 17, wherein the double bond between C9 and C10 is in a E configuration.

20. The compound of claim 3, wherein $R_3$ is —$CH_3$, $R_4$ is hydrogen, the double bond is absent between C10 and $R_3$, the double bond is absent between C1 and C10, the double bond is absent between C9 and C10, and the double bond is absent between C3 and C4.

21. The compound of claim 20, wherein said compound is in an R configuration at C10.

22. The compound of claim 20, wherein said compound is in an S configuration at C10.

23. The compound of claim 3, wherein $R_3$ is —$CH_3$, the double bonds are absent between $R_3$ and C10, C1 and C10, and C9 and C10, the double bond is also absent between C3 and C4, $R_7$ is hydrogen, $R_4$ is an oxygen atom, and $R_4$ together with C3 and C10 to which it attached and C1 and C2 constitute a 5 membered tetrahydrofuran ring.

24. The compound of claim 23, wherein said compound is in an R configuration at C3.

25. The compound of claim 23, wherein said compound is in an S configuration at C3.

26. The compound of claim 4, wherein $R_3$ is —$CH_3$ and the double bond is absent between C10 and $R_3$, the double bond is absent between C1 and C10, the double bond is absent between C9 and C10, and the double bond is present between C3 and C4.

27. The compound of claim 26, wherein the compound is in an R configuration at C10.

28. The compound of claim 26, wherein the compound is in an S configuration at C10.

29. The compound of claim 4, wherein $R_3$ is —$CH_3$ and the double bond is absent between C10 and $R_3$, the double bond is absent between C1 and C10, the double bond is absent between C9 and C10, and the double bond is absent between C3 and C4.

30. The compound of claim 29, wherein the compound is in an R configuration at C10.

31. The compound of claim 29, wherein the compound is in an S configuration at C10.

32. The compound of claim 4, wherein $R_3$ is —$CH_3$, the double bonds are absent between $R_3$ and C10, C1 and C10, and C9 and C10, the double bond is also absent between C3 and C4, and $R_7$ is —OMe.

33. The compound of claim 32, wherein said compound is in an R configuration at C3.

34. The compound of claim 32, wherein said compound is in an S configuration at C3.

35. The compound of claim 5, wherein said compound is in an R configuration at C3.

36. The compound of claim 5, wherein said compound is in an S configuration at C3.

37. A compound selected from the group consisting of:
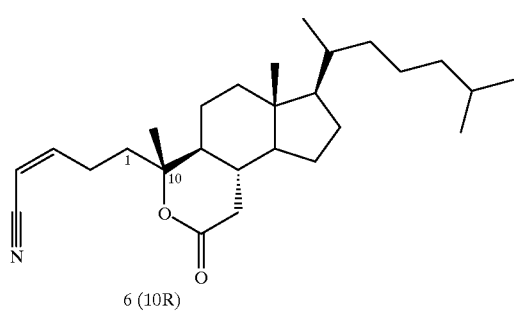
6 (10R)
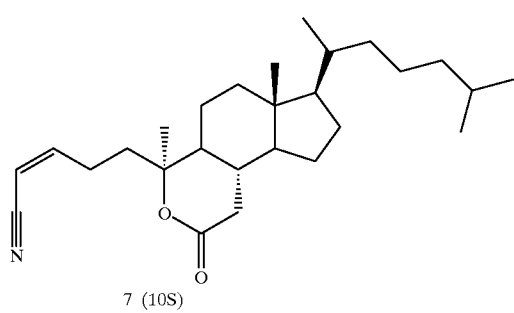
7 (10S)
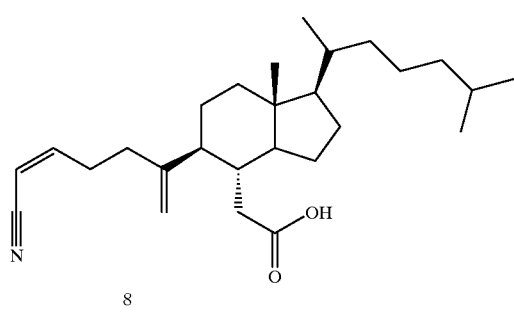
8
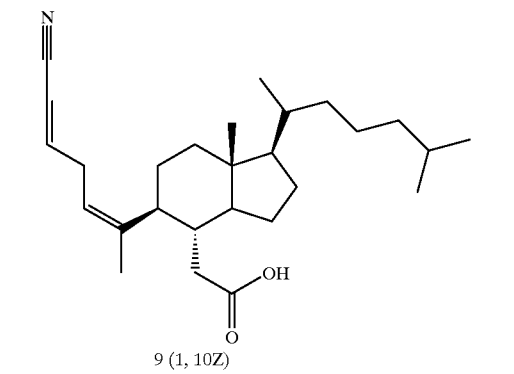
9 (1, 10Z)
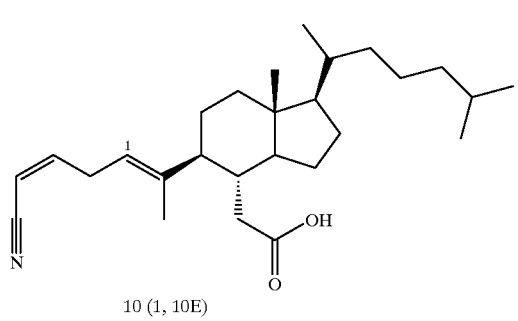
10 (1, 10E)
-continued
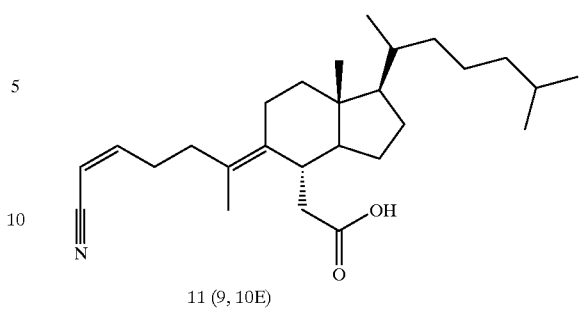
11 (9, 10E)
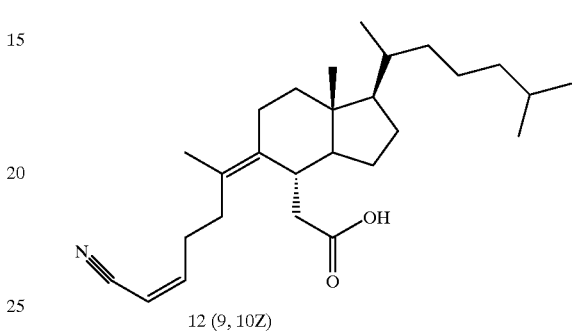
12 (9, 10Z)
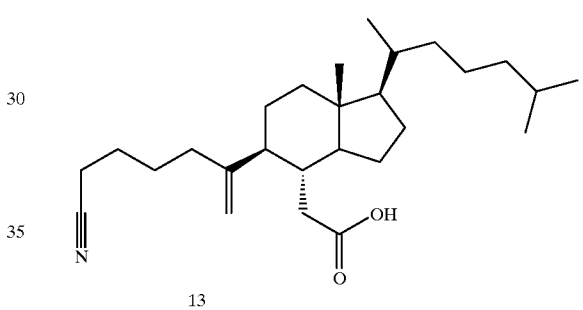
13
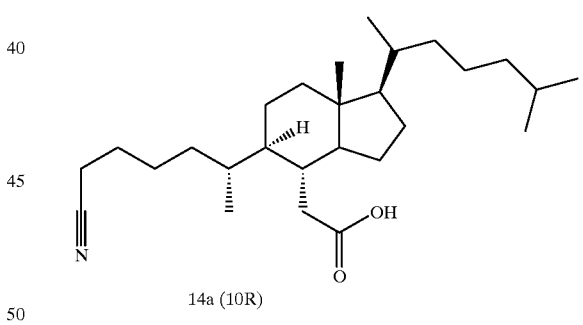
14a (10R)
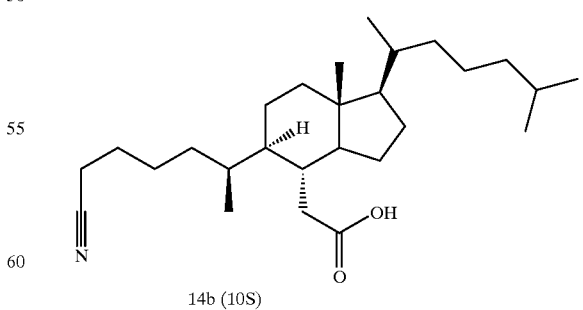
14b (10S)

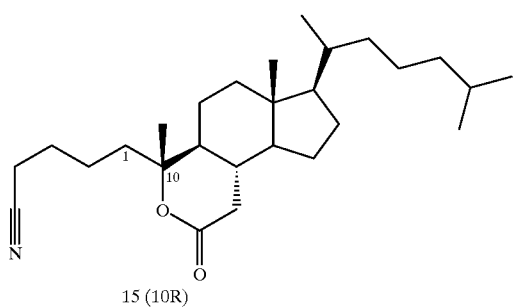
15 (10R)
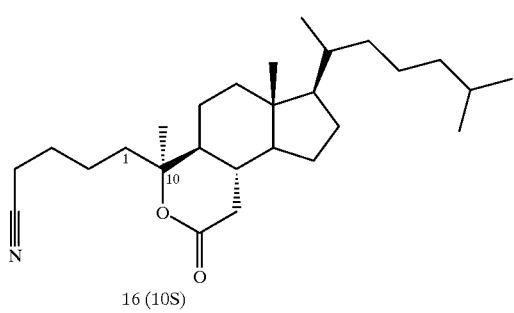
16 (10S)
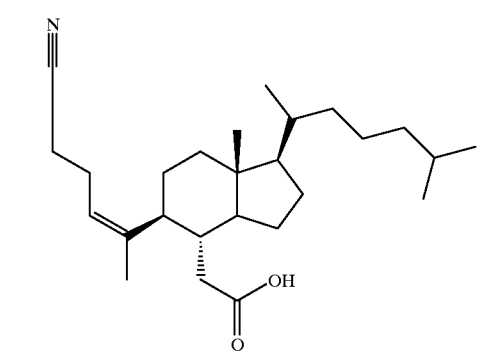
17 (1, 10Z)
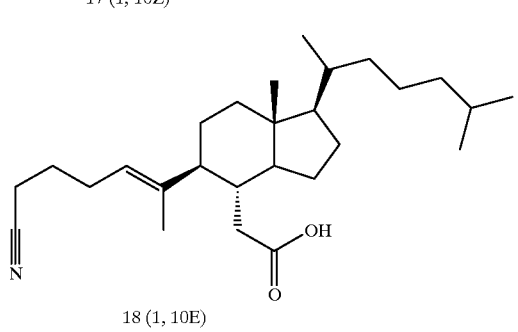
18 (1, 10E)
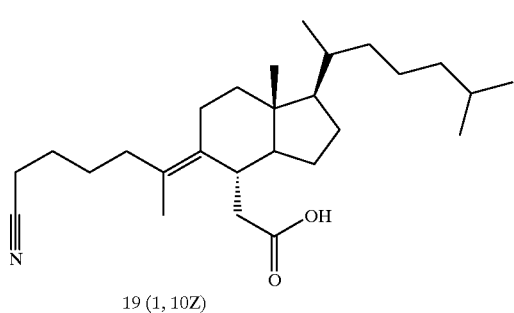
19 (1, 10Z)
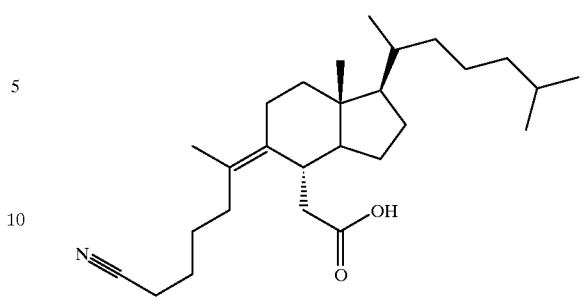
20 (9, 10Z)
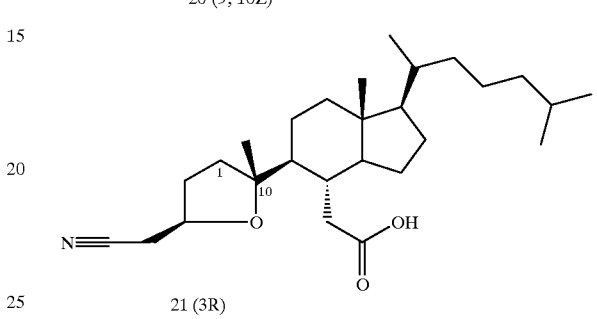
21 (3R)
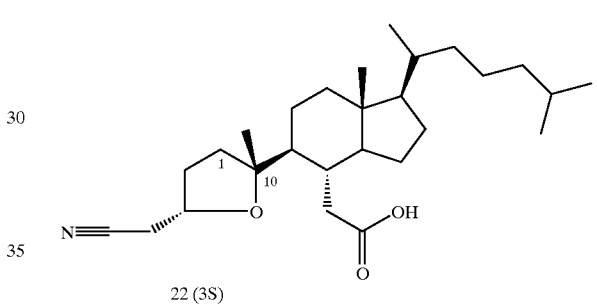
22 (3S)
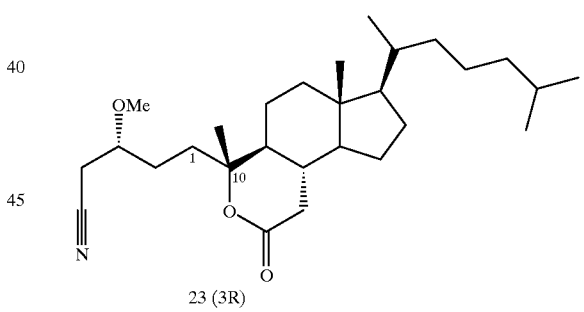
23 (3R)
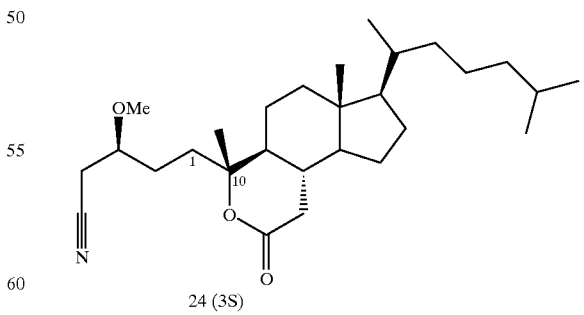
24 (3S)

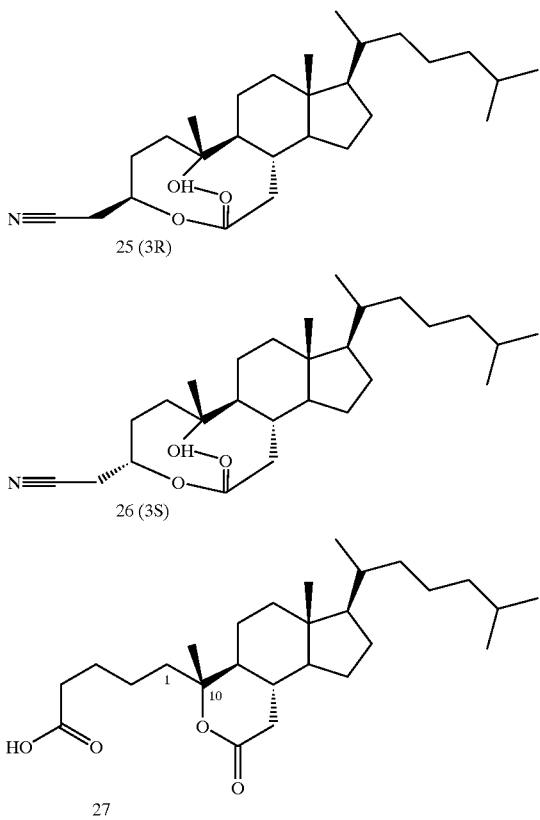

and pharmaceutically acceptable salts thereof.

38. A method of making cholestane derivatives, comprising:

heating a compound of the formula

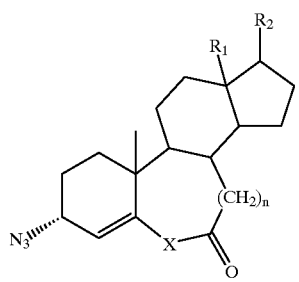

wherein:

R₁ is selected from the group consisting of H, lower alkyl, and alkoxy;

R₂ is selected from the group consisting of C1–C10 alkyl, substituted C1–C10 alkyl, C2–C10 alkene containing one to four double bonds, substituted C2–C10 alkene, and C1–C10 alkyl or C2–C10 alkene having one or more heteroatoms selected from the group consisting of oxygen atoms and nitrogen atoms inserted into the chain thereof, the chain having 10 or less atoms including the hetero atoms;

n is an integer from 1 to 3; and

X is oxygen or nitrogen, under conditions sufficient to form at least one compound of formula (I)

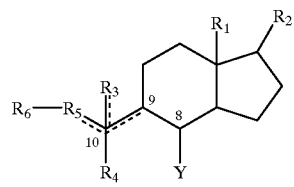

wherein:

R₁ and R₂ have the meanings ascribed above;

R₃ is selected from the group consisting of methylene, ketone, and methyl;

R₄ is absent when R₃ is methylene or ketone, or R₄ is selected from the group consisting of hydrogen, lower alkyl, alkoxy, lower alkanoyloxy, hydroxy, carboxyl, amino, lower alkylamino, and halo when R₃ is methyl;

Y is selected from the group consisting of C1–C6 alkyl or C2–C6 alkene terminating in an amide group —CONH₂, a nitrile group —CN, or an acid group, or a salt thereof, or Y is —(CH₂)ₙ—C(O)—X—, wherein n is an integer from 1 to 3, X is oxygen or nitrogen, and together with C8 atom to which Y is attached, the C9 atom, and the C10 atom constitute a ring system comprising a 6 to 8 membered lactone or lactam ring;

R₅ is C4 alkyl or alkene;

R₆ is CN; and the broken lines indicate optional double bonds, and pharmaceutically acceptable salts thereof, optionally modifying the chain length between C10 and CN to provide a C2–C8 alkyl, C2–C8 alkene having one or more double bonds, substituted C2–C8 alkyl, or substituted C2–C8 alkene; and optionally reacting CN with a functionalizing agent to modify CN to a functional group selected from the group consisting of COOH, CSSH, or salts of these acid groups CHO, CH₂OH, CONH₂, and CONR₂, wherein R is lower alkyl, acyl or H, or to replace CN and a hydrogen atom of a carbon atom adjacent CN with identical functional groups.

39. The method of claim 38, wherein n is 1 and X is oxygen.

40. The method of claim 38, wherein said heating step is conducted on a silica gel substrate.

41. The method of claim 38, wherein said heating step is conducted at a temperature ranging from about 100 to about 250° C.

42. The method of claim 41, wherein said heating step is conducted at a temperature of about 180° C.

43. The method of claim 39, wherein said product comprises a mixture of compounds of formula (I), and wherein said process further comprises recovering said compounds.

44. The method of claim 43, further comprising the step of saturating at least one double bond of at least one of said recovered compounds.

45. The method of claim 43, further comprising the step of base catalyzed hydrolysis and Michael addition of at least one of the said recovered compounds.

46. A pharmaceutical formulation comprising a compound of the formula (I)

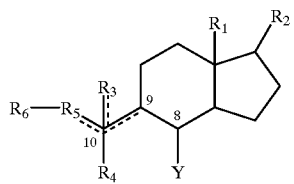

wherein:

- R₁ is selected from the group consisting of H, lower alkyl, and alkoxy;
- R₂ is selected from the group consisting of C1–C10 alkyl, substituted C1–C10 alkyl, C2–C10 alkene containing one to four double bonds, substituted C2–C10 alkene, and C1–C10 alkyl or C2–C10 alkene having one or more heteroatoms selected from the group consisting of oxygen atoms and nitrogen atoms inserted into the chain thereof, the chain having 10 or less atoms including the hetero atoms;
- R₃ is selected from the group consisting of methylene, ketone, and methyl;
- R₄ is absent when R₃ is methylene or ketone, or when R₃ is methyl, R₄ is selected from the group consisting of hydrogen, lower alkyl, alkoxy, lower alkanoyloxy, hydroxy, carboxyl, amino, lower alkylamino, and halo, or R₄ is an oxygen atom and together with the C10 atom to which R₄ is attached and R₅ comprises a heterocyclic ring and the double bond between C10 and R₃, C9 and C10, or C10 and R₅ is absent;
- Y is selected from the group consisting of C1–C6 alkyl or C2–C6 alkene terminating in an amide group —CONH₂, a nitrile group —CN, or an acid group selected from the group consisting of carboxylic acids, sulfonic acids, carbodithioic acids, and phosphoric acids, or salts thereof, or
- Y is —(CH₂)ₙ—C(O)—X—, wherein n is an integer from 1 to 3, X is oxygen or nitrogen, and together with C8 atom to which Y is attached, the C9 atom, and the C10 atom constitute a ring system comprising a 6 to 8 membered lactone or lactam ring, or
- Y is —(CH₂)—C(O)—O—, and together with the C8 atom to which Y is attached, the C9 atom, the C10 atom, and R₅ constitute a ring system comprising a lactone ring when R₃ is methyl, R₄ is hydroxyl and the double bond between C10 and R₃, R₅ and C10 or C9 and C10 is absent;
- R₅ is selected from the group consisting of C2–C8 alkyl, C2–C8 alkene having one or more double bonds, substituted C2–C8 alkyl, and substituted C2–C8 alkene;
- R₆ is a functional group selected from the group consisting of CN, COOH, CSSH, or salts of these acid groups, CHO, CH₂OH, CONH₂, and CONR₂, wherein R is lower alkyl, acyl or H, and optionally a hydrogen atom of a carbon atom adjacent R₆ is replaced with an identical functional group; and
- the broken lines indicate optional double bonds, or a pharmaceutically acceptable salt thereof in a pharmaceutically acceptable carrier.

47. The pharmaceutical formulation of claim 46, wherein n is 1 and X is oxygen.

48. The compound of claim 3, wherein R₁ is —CH₃, R₂ is —CH(CH₃)(CH₂)₃CH(CH₃)₂, and R₆ is —CN.

* * * * *